(12) United States Patent
Chen et al.

(10) Patent No.: US 11,414,411 B2
(45) Date of Patent: Aug. 16, 2022

(54) CHEMICAL PROCESS FOR MANUFACTURING MONOBACTAM ANTIBIOTIC AND INTERMEDIATES THEREOF

(71) Applicant: Novartis AG, Basel (CH)

(72) Inventors: Like Chen, Changshu (CN); Chi Ming Cheung, Changshu (CN); Zhongbo Fei, Changshu (CN); Qun Jiang, Changshu (CN); Lei Li, Changshu (CN); Bin Li, Changshu (CN); Thomas Ruch, Basel (CH); Hao Wang, Changshu (CN); Quanbing Wu, Changshu (CN)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 16/635,596

(22) PCT Filed: Aug. 1, 2018

(86) PCT No.: PCT/IB2018/055789
§ 371 (c)(1),
(2) Date: Jan. 31, 2020

(87) PCT Pub. No.: WO2019/026004
PCT Pub. Date: Feb. 7, 2019

(65) Prior Publication Data
US 2020/0239461 A1    Jul. 30, 2020

(30) Foreign Application Priority Data

Aug. 2, 2017 (WO) ................ PCT/CN2017/095617

(51) Int. Cl.
*C07D 417/14* (2006.01)
(52) U.S. Cl.
CPC .................................. *C07D 417/14* (2013.01)
(58) Field of Classification Search
CPC .................................................. C07D 417/14
See application file for complete search history.

(56) References Cited

U.S. PATENT DOCUMENTS

| | | | |
|---|---|---|---|
| 4,775,670 A | 10/1988 | Sykes et al. | |
| 4,782,147 A | 11/1988 | Ochiai et al. | |
| 5,112,968 A | 5/1992 | Treuner | |
| 9,174,978 B2 | 11/2015 | Aulakh et al. | |
| 9,238,657 B2 | 1/2016 | Nishitani et al. | |
| 10,369,138 B2 | 8/2019 | Aulakh et al. | |
| 2011/0190254 A1 | 8/2011 | Nishitani et al. | |
| 2012/0302542 A1 | 11/2012 | Brown et al. | |

FOREIGN PATENT DOCUMENTS

| | | |
|---|---|---|
| CL | 19810097302 | 12/1981 |
| CL | 201401956 | 11/2014 |
| CL | 201602285 | 12/2016 |
| CN | 103044416 A | 4/2013 |
| CN | 106164072 A | 11/2016 |
| EA | 030850 B1 | 10/2018 |
| EP | 0048953 A2 | 4/1982 |
| EP | 0053816 A1 | 6/1982 |
| EP | 0073061 A2 | 3/1983 |
| EP | 0083039 A1 | 7/1983 |
| EP | 0093376 A2 | 11/1983 |
| EP | 0095778 A1 | 12/1983 |
| EP | 0096297 A2 | 12/1983 |
| EP | 0177940 A2 | 4/1986 |
| JP | S61-53282 A | 3/1986 |
| JP | S61-53283 A | 3/1986 |
| JP | 2013-544276 A | 12/2013 |
| NL | 8100571 A | 9/1981 |
| WO | WO-2010/050468 A1 | 5/2010 |
| WO | WO-2010/070523 A1 | 6/2010 |
| WO | WO-2012/073138 A1 | 6/2012 |
| WO | WO-2013/110643 A1 | 8/2013 |
| WO | WO-2015/103583 A1 | 7/2015 |
| WO | WO-2015/148379 A1 | 10/2015 |
| WO | WO-2017/050218 A1 | 3/2017 |

OTHER PUBLICATIONS

International Search Report for International Application No. PCT/IB2018/055789, dated Feb. 8, 2019 (5 pages).
Written Opinion of the International Searching Authority for International Application No. PCT/IB2018/055789, dated Feb. 8, 2019 (10 pages).
International Preliminary Report on Patentability for International Application No. PCT/IB2018/055789, dated Feb. 4, 2020 (11 pages).
Berge et al., "Pharmaceutical salts," J Pharm Sci. 66(1):1-19 (1977).
English language translation of Official Action for Russian Application No. 2018114480/04(022642) dated Jun. 9, 2020 (9 pages).
Extended European Search Report for European Patent Application No. 16848099.4 dated May 27, 2019 (10 pages).
Floyd et al., "Monobactams. Stereospecific synthesis of (S)-3-amino-2-oxoazetidine-1-sulfonic acids," J Org Chem. 47:176-178 (1982).

(Continued)

*Primary Examiner* — Paul V Ward
(74) *Attorney, Agent, or Firm* — Clark & Elbing LLP

(57) ABSTRACT

The present invention provides a process of synthesizing 1-(((Z)-(1-(2-aminothiazol-4-yl)-2-oxo-2-(((3S,4R)-2-oxo-4-((2-oxooxazolidin-3-yl)methyl)-1-sulfoazetidin-3 yl)amino)ethylidene)amino)oxy)cyclopropanecarboxylic acid (referred to herein as Compound X), or a salt thereof, or a solvate including hydrate thereof, and/or intermediates thereof, and the use of intermediates for preparing Compound X. In particular, the process relates to the preparation of Compound X using dynamic kinetic resolution (DKR) and asymmetric catalytic reduction, thereby providing an improved route to 1-(((Z)-(1-(2-aminothiazol-4-yl)-2-oxo-2-(((3S,4R)-2-oxo-4-((2-oxooxazolidin-3-yl)methyl)-1-sulfoazetidin-3 yl)amino)ethylidene)amino)oxy)cyclopropanecarboxylic acid (Compound X) and compositions containing said compound, including the arginine salt, sodium salt and hydrated solid forms of Compound X.

17 Claims, 1 Drawing Sheet

(56) References Cited

OTHER PUBLICATIONS

Fryer et al., "Addition of glycinate enolate equivalents to 1,4-benzodiazepine imino phosphates. Preparation of synthetically useful 2-(ethyl glycinat-.alpha.-ylidene)-1,4-benzodiazepines and related derivatives," J Org Chem. 56(11):3715-3719 (1991).
Guzman et al., "Tight regulation, modulation, and high-level expression by vectors containing the arabinose PBAD promoter," J Bacteriol. 177(14):4121-30 (1995).
Haldimann et al., "Conditional-replication, integration, excision, and retrieval plasmid-host systems for gene structure-function studies of bacteria," J Bacteriol. 183(21):6384-93 (2001).
Kitamura et al., "Quantitative Expression of Dynamic Kinetic Resolution of Chirally Labile Enantiomers: Stereoselective Hydrogenation of 2-Substituted 3-Oxo Carboxylic Esters Catalyzed by BINAP-Ruthenium(II) Complexes," J Am Chem Soc. 115:144-152 (1993).
Mastalerz et al., "An examination of O-2-isocephems as orally absorbable antibiotics," J Med Chem. 31(6):1190-6 (1988).
Matt et al., "C-Alkylation of Peptides Containing Aminomalonate) and (Amino)(cyano)acetate Residues," Helvetica Chimica Acta 81:1845-1895 (1998).
Morissette et al., "High-throughput crystallization: polymorphs, salts, co-crystals and solvates of pharmaceutical solids," Adv Drug Deliv Rev. 56(3):275-300 (2004).
Noriaki Hirayama, "Handbook for preparing crystals of organic compounds—Principles and know-how," pp. 17-23, 37-40, 45-51, 57-65 (2008) (28 pages).
Noriyuki Takata, "API form screening and selection in drug discovery stage," Pharm Stage. 6(10):20-25 (2007) (8 pages).
English language translation of the Notice on the First Office Action for Chinese Patent Application No. 201680055680.4 dated Sep. 23, 2020 (11 pages).
Office Action for Chilean Patent Application No. 201800745 dated Aug. 14, 2019 (13 pages) (English language translation not available).
Office Action for Japanese Patent Application No. 2018-515607 dated Aug. 25, 2020 (9 pages).
Wu et al., "Design, synthesis and antibacterial activities of a series of new 2-oxaisocephems," Bioorg Med Chem Lett. 22(16):5293-6 (2012) . . . .
Yusaku Shioji, "Manufacture Technology of Solid Tablet," CMC. pp. 9, 12-13 (2003) (4 pages).
Matsuda et al., "Preferential Hydrolysis of cis Configuration Compounds at the 3,4 Position of Monobactams by Beta-Lactamase from Morganella Morganii," Antimicrob Agents Chemother. 35(3):458-461 (1991).
Sendai et al., "Chemical Modification of Sulfazecin Synthesis of 4-(Substituted Methyl)-2-Azetidinone-1-Sulfonic Acid Derivatives," J Antibiotics. 38(3):346-71 (1985).
Matsuda et al., "Structure-Activity Relations of 4-Fluoromethyl Monobactams" J Antimicrob Chemother. 19(6):753-760 (1987).
Page, "Siderophore Conjugates," Ann N Y Acad Sci. 1277:115-26 (2013).
Neu et al., "In vitro Activity and Beta-Lactamase Stability of a new Monobactam, B0-1165," Antimicrob Agents Chemother. 31(4):505-11 (1987).
Tomaras et al., "Adaption-Based Resistance to Siderophore-Conjugated Antibacterial Agents by Pseudomonas aeruginosa," Antimicrob Agents Chemother. 57(9):4197-4207 (2013).
Reck et al., "Synthesis and Optimization of Novel Monobactams with Activity Against Carbapenem-Resistant Enterobacteriaceae: Identification of LYS228," ASM Microbe, Jun. 1-5, 2017, New Orleans, LA. Poster Saturday—297 (2017).
Brown et al., "Pyridone-conjugated monobactam antibiotics with gram-negative activity," J Med Chem. 56(13):5541-52 (2013).
Uri, "High Degree of Specificity of the Color Reaction for the Aminothiazolyl Oxyimino Beta-Lactam Antibiotics," Acta Chimica Hungarica. 128(1):89-91 (1991).
Caira, "Crystalline polymorphism of organic compounds," Topics in Current Chemistry 198:163-208 (1998).

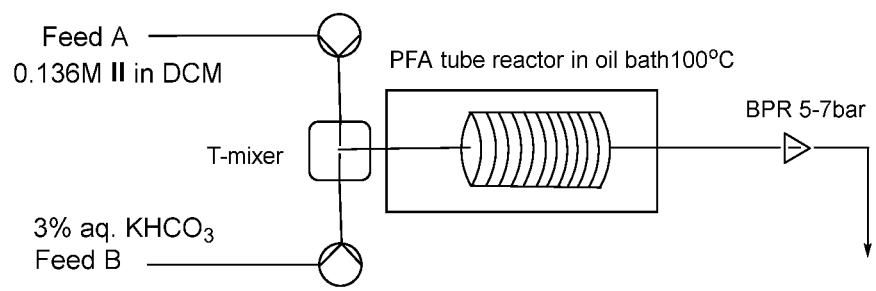

CHEMICAL PROCESS FOR MANUFACTURING MONOBACTAM ANTIBIOTIC AND INTERMEDIATES THEREOF

FIELD OF THE INVENTION

The present invention relates to processes, process steps and intermediates useful in the preparation of monobactam antibiotic 1-(((Z)-(1-(2-aminothiazol-4-yl)-2-oxo-2-(((3S, 4R)-2-oxo-4-((2-oxooxazolidin-3-yl)methyl)-1-sulfoazetidin-3-yl)amino)ethylidene)amino)oxy)cyclopropanecarboxylic acid (Compound X), or a salt thereof, or a solvate including hydrate thereof. The present invention also relates to intermediates useful in such processes.

BACKGROUND

Over the past several decades, the frequency of antimicrobial resistance and its association with serious infectious diseases have increased at alarming rates. The increasing prevalence of resistance among nosocomial pathogens is particularly disconcerting. Of the over 2 million (hospital-acquired) infections occurring each year in the United States, 50 to 60% are caused by antimicrobial-resistant strains of bacteria. The high rate of resistance to commonly used antibacterial agents increases the morbidity, mortality, and costs associated with nosocomial infections. In the United States, nosocomial infections are thought to contribute to or cause more than 77,000 deaths per year and cost approximately $5 to $10 billion annually.

Important causes of Gram-negative resistance include extended-spectrum 13-lactamases (ESBLs), serine carbapenemases (KPCs) and metallo-13-lactamases (for example NDM-1) in *Klebsiella pneumoniae, Escherichia coli*, and *Proteus mirabilis*, high-level third-generation cephalosporin (AmpC) 13-lactamase resistance among *Enterobacter* species and *Citrobacter freundii*, and multi-drug-resistance genes observed in *Pseudomonas, Acinetobacter*, and *Stenotrophomonas*. The problem of antibacterial resistance is compounded by the existence of bacterial strains resistant to multiple antibacterials. For example, *Klebsiella pneumonia* harboring NDM-1 metallo-13-lactamase carries frequently additional serine-13-lactamases on the same plasmid that carries the NDM-1.

Thus there is a need for new antibacterials, particularly antibacterial compounds that are effective against existing drug-resistant microbes, or are less susceptible to development of new bacterial resistance. Monobactam antibiotic, which is referred to herein as Compound X, is primarily effective against Gram-negative bacteria, including strains that show resistance to other monobactams.

The present invention relates to a process for the preparation of monobactam antibiotic Compound X and intermediates thereof.

More particularly, the present invention relates to a process for the preparation of Compound X

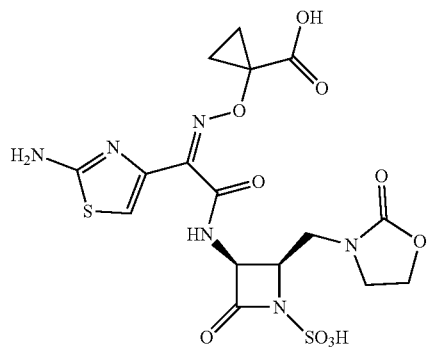

Compound X also referred to as 1-(((Z)-(1-(2-aminothiazol-4-yl)-2-oxo-2-(((3S,4R)-2-oxo-4-((2-oxooxazolidin-3-yl)methyl)-1-sulfoazetidin-3-yl)amino)ethylidene)amino)oxy)cyclopropanecarboxylic acid, or a salt thereof, or a solvate including hydrate thereof.

Patent application number PCT/US2015/022011 describes certain monobactam antibiotics. Compound X may be prepared using the method disclosed in PCT/US2015/022011, in particular example 22, and in PCT/CN2016/099482.

A drawback from these processes is that they exhibit a large number of process steps and intermediate nitrogen protection/deprotection steps, reducing the overall yield and efficiency. Furthermore, these processes require several chromatographic purification steps to be carried out in course of the processes. We have found that the preparation of Compound X, as previously prepared on a manufacturing scale, possesses a number of disadvantages, in particular poor handling characteristics.

It would thus be beneficial to develop alternative or improved processes for the production of Compound X that do not suffer from some or all of these disadvantages.

BRIEF DESCRIPTION OF THE DRAWING

FIG. 1 is a schematic diagram illustrating the synthesis of compound (IA)).

BRIEF DESCRIPTION

The present invention is thus directed to a new process for the synthesis of Compound X in a shorter time, and in an improved, more economic and simplified fashion. In particular, the new improved process provides a manufacturing advantage in that the need for nitrogen protecting groups is eliminated in the final steps of the synthesis of Compound X, compared to the routes previously disclosed in patent applications PCT/US2015/022011 and PCT/CN2016/099482. Thus, in a first aspect, the present invention provides a concise end-game without the need for protecting groups. Specific aspects of the present invention can be applied to preparing Compound X, or a salt thereof, or a solvate including hydrate thereof, as well as useful intermediates such as compounds of the formula (VIIc), (IV), (III), (II), (I), particularly the compound of formula (IA), and compounds 4, 22, 2A.

In accordance with a first aspect of the invention there is provided a process for the preparation of Compound X or a salt thereof, or a solvate including hydrate thereof, comprising the step of reacting a compound of formula 22, or a salt thereof, with a compound of formula 2A, or a salt thereof:

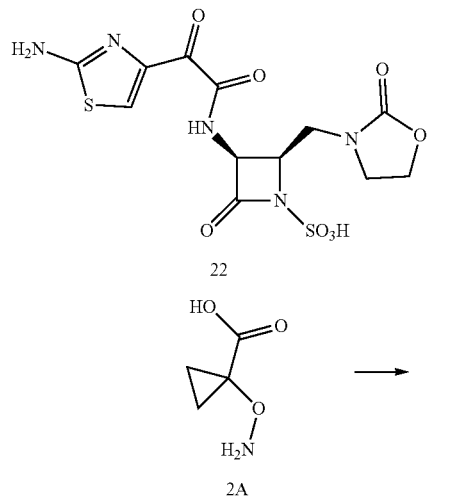

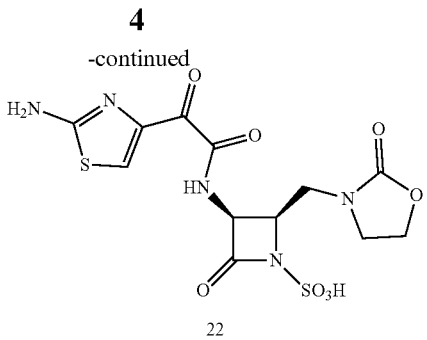

in the presence of a solvent, with a base and a coupling agent, wherein M⁺ is hydrogen or a salt forming cation.

In accordance with a further aspect of the invention there is provided a process for the preparation of Compound X or a salt thereof, or a solvate including hydrate thereof, comprising the process of preparing compound 22, or a salt thereof, from a compound of formula 21 and (IB), and reacting compound 22 with compound 2A.

In accordance with a further aspect of the invention there is provided a process for the preparation of a compound of formula (IV)

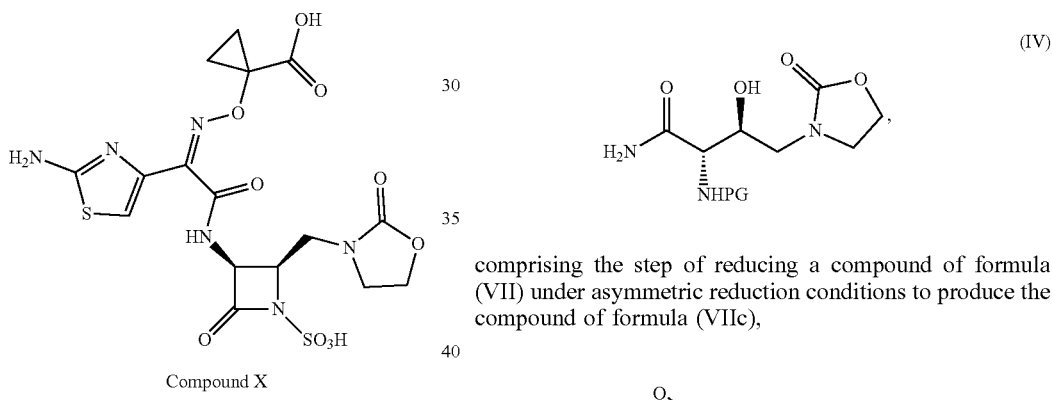

comprising the step of reducing a compound of formula (VII) under asymmetric reduction conditions to produce the compound of formula (VIIc),

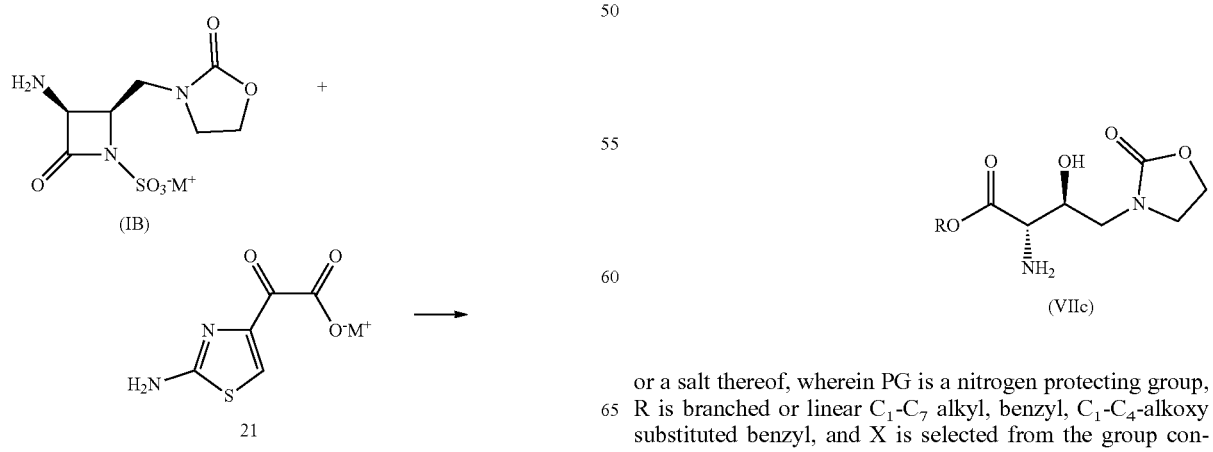

or a salt thereof, wherein PG is a nitrogen protecting group, R is branched or linear $C_1$-$C_7$ alkyl, benzyl, $C_1$-$C_4$-alkoxy substituted benzyl, and X is selected from the group consisting of halide, carboxylate, and sulfonate.

In accordance with a further aspect of the invention there is provided a process for the preparation of a compound of formula (I)

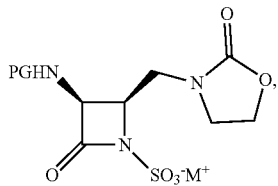
(I)

comprising the process of preparing a compound of formula (IV), or a salt thereof, further comprising the steps of (iv) converting a compound of formula (IV) to a compound of formula (III),

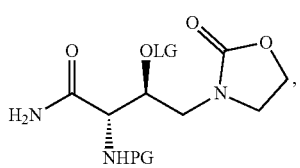
(III)

wherein PG is a nitrogen protecting group, LG is —SO₂T, wherein T is selected from C₄F₉, CF₃, F, C₆H₄CH₃, CH₃, C₆H₆, (v) reacting a compound of formula (III), in a solvent with a base, followed by addition of a halosulfonic acid, preferably chlorosulfonic acid, and a salt forming reagent, to produce a compound of formula (II),

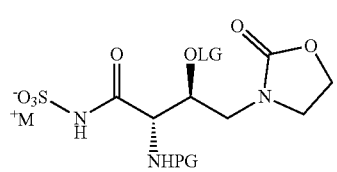
(II)

wherein M⁺ is hydrogen or a salt forming cation, and LG and PG are as defined for a compound of formula (III), (vi) reacting a compound of formula (II) in a solvent with a base, preferably under flow preparation conditions, to produce a compound of formula (I).

In accordance with a further aspect of the invention there is provided a process for the preparation of Compound X, or a salt thereof, or a solvate including hydrate thereof, comprising the process of preparing a compound of formula (I).

In accordance with a further aspect of the invention there is provided a process for preparing Compound X, or a salt thereof, or a solvate including hydrate thereof, the process comprising the steps of:

(a-1) preparing

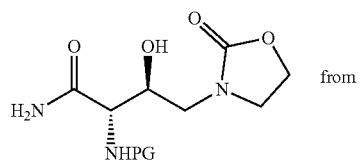
(IV)

from

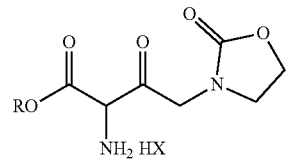
(VII)

(b-1) preparing

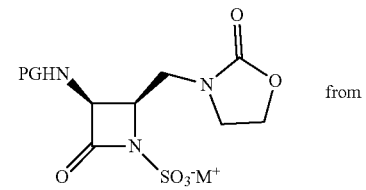
(I)

from

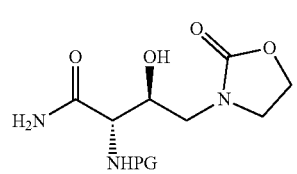
(IV)

(c-1) reacting

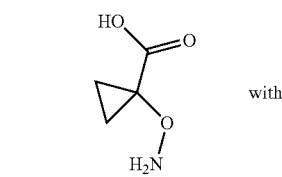
2A with

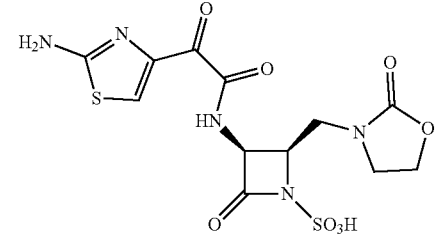
22 to form Compound X.

In accordance with a further aspect of the invention there is provided a process for preparing Compound X, or a salt thereof, or a solvate including hydrate thereof, the process comprising the steps of:

(a) preparing

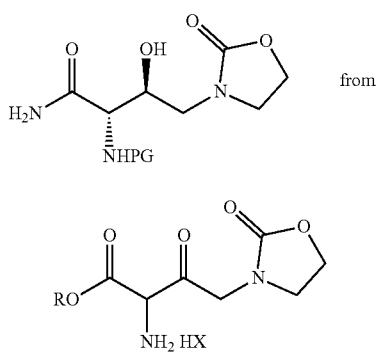

from

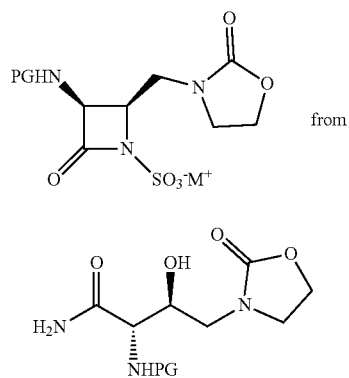

(b) preparing

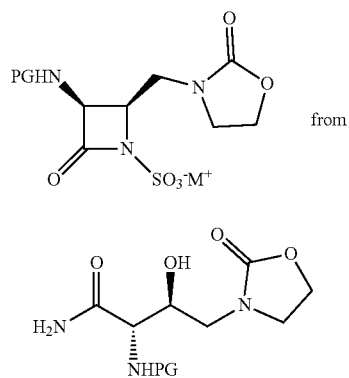

from

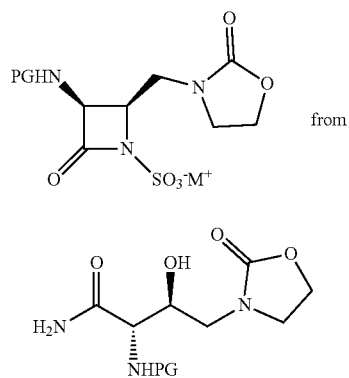

(c) reacting with

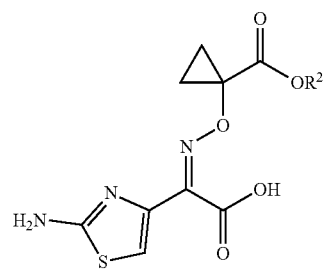

to form

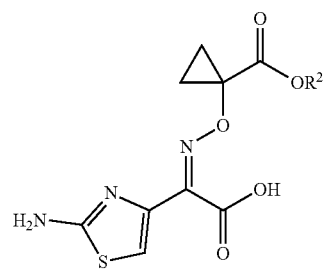

(IV)

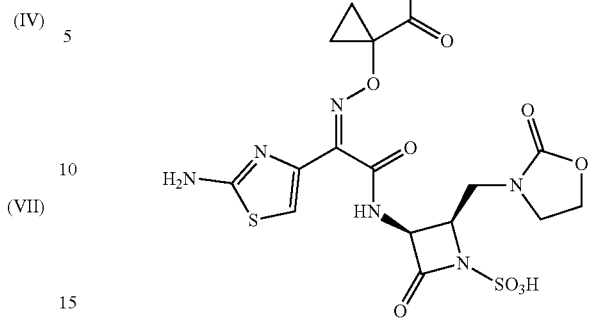

(VII)

(d) deprotecting a compound of formula (4) with an acid to remove R², to obtain Compound X.

A further aspect of the invention provides the use of a compound of formula (IV) in the preparation of Compound X, or a salt thereof, or a solvate including hydrate thereof.

A further aspect of the invention provides the use of a compound of formula (I), preferably of formula (IA), in the preparation of Compound X, or a salt thereof, or a solvate including hydrate thereof.

Yet another aspect of the invention is the compound of formula (IV)

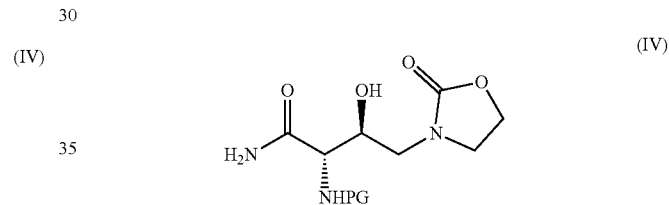

wherein PG is a nitrogen protecting group.

Another aspect of the invention is the compound of formula (VII)

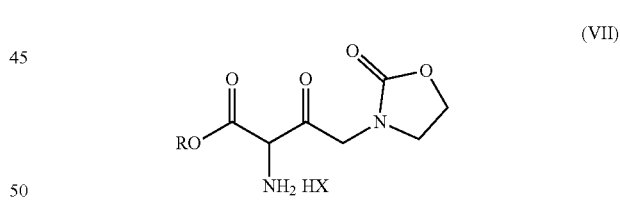

wherein R is branched or linear $C_1$-$C_7$-alkyl, benzyl, $C_1$-$C_4$-alkoxy substituted benzyl, and X is selected from the group consisting of halide, carboxylate, and sulfonate.

Another aspect of the invention is the compound of formula (IV-B)

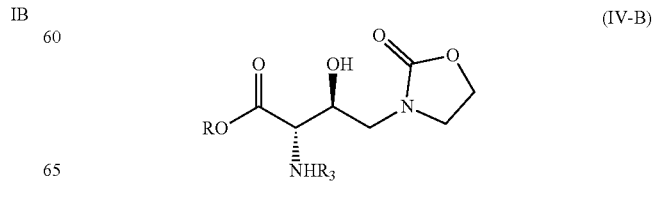

wherein R is branched or linear $C_1$-$C_7$-alkyl, benzyl, $C_1$-$C_4$-alkoxy substituted benzyl and $R_3$ is selected from H, PG, wherein PG is a nitrogen protecting group.

Another aspect of the invention is the compound of formula (IV-C)

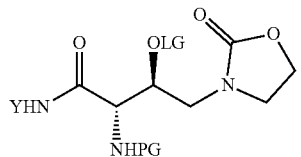
(IV-C)

wherein LG and PG are as defined herein and Y is selected from H, $SO_3^-M^+$, wherein $M^+$ is hydrogen or a salt forming cation.

Another aspect of the invention is the compound of formula (IA)

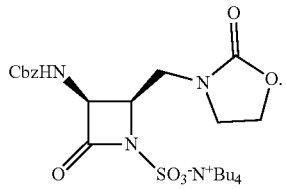
(IA)

In another aspect, there is a compound of formula (4)

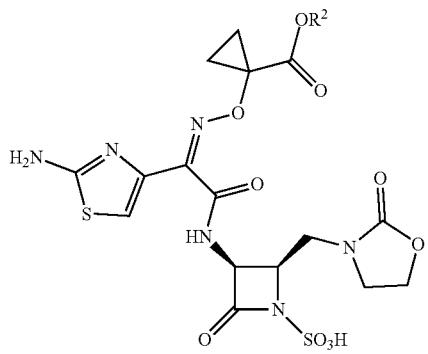
4 wherein $R^2$ is selected from branched or linear $C_1$-$C_7$-alkyl, benzyl, $C_1$-$C_4$-alkoxy substituted benzyl, $CH(aryl)_2$, preferably $R_2$ is $CH(aryl)_2$, more preferably $CH(C_6H_5)_2$.

In another aspect, there is a compound of formula (22)

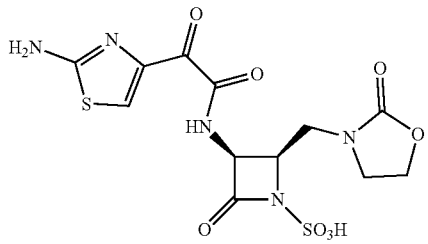
22 or a salt thereof.

In another aspect, there is a compound of formula (2A)

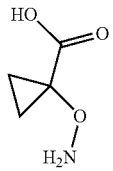
2A or a salt thereof.

DETAILED DESCRIPTION

The process(es) according to the present invention, for producing Compound X, or a salt thereof, or a solvate including hydrate thereof, and/or intermediates, as defined herein, are summarized in Scheme 1.

The present inventors have found that surprisingly, Compound X may be assembled without the need for nitrogen protecting groups to protect reactive nitrogen functionalities, in the final steps of the processes, by reacting the compound of formula 22 with the compound of formula 2A, to obtain Compound X. Thus, the present invention provides a concise end-game without the need of protecting groups, and also reduces the need to use chromatography for purification of intermediates.

Thus, in another aspect, the present invention provides compound 22 which is a very useful intermediate in this new, inventive process of synthesizing Compound X, as well as methods to convert Compound 22 into Compound X.

Scheme 1

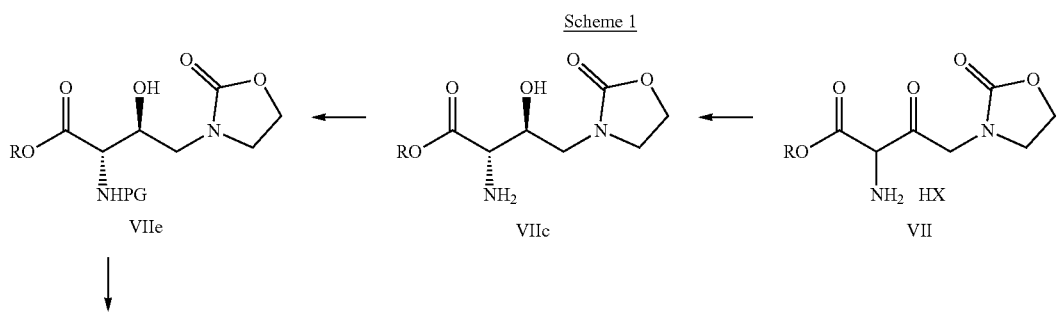

11
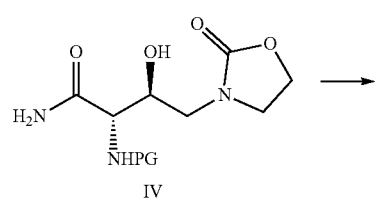 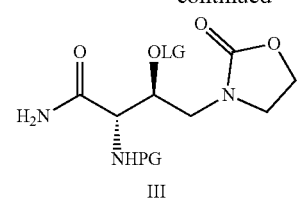 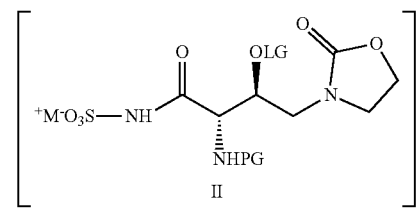
12
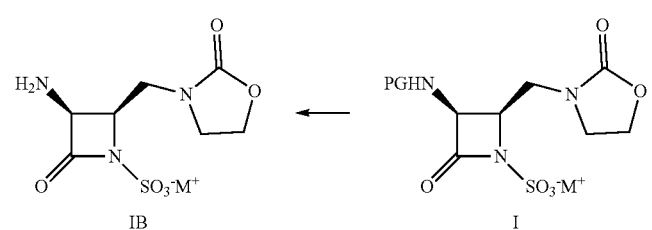
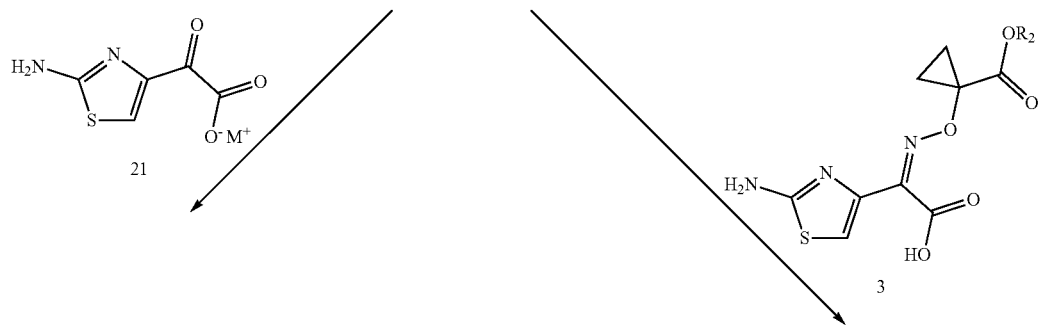
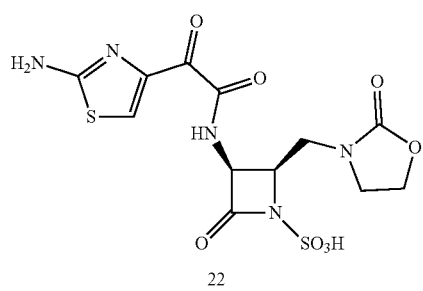
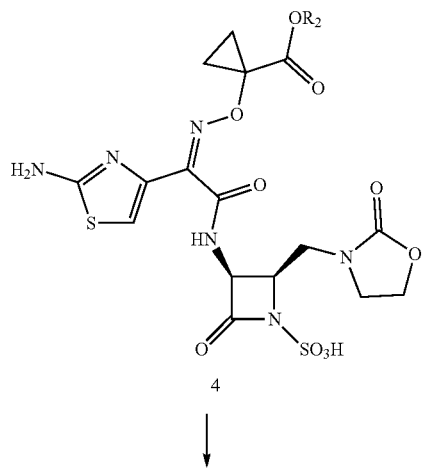
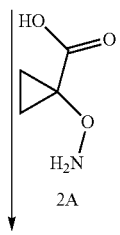
Compound X
Compound X Preparation of Compound X from Intermediates 22 and 2A This section relates to a process for the manufacture of Compound X, wherein the compound of formula (22) is reacted with the compound of formula (2A).

Accordingly, a first aspect of the present invention relates to a process for the preparation of Compound X Compound X

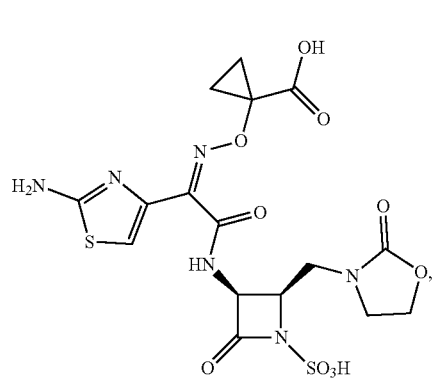

comprising the step of reacting the compound of formula 22, or a salt thereof, with the compound of formula (2A), as defined in Scheme 2.

Scheme 2

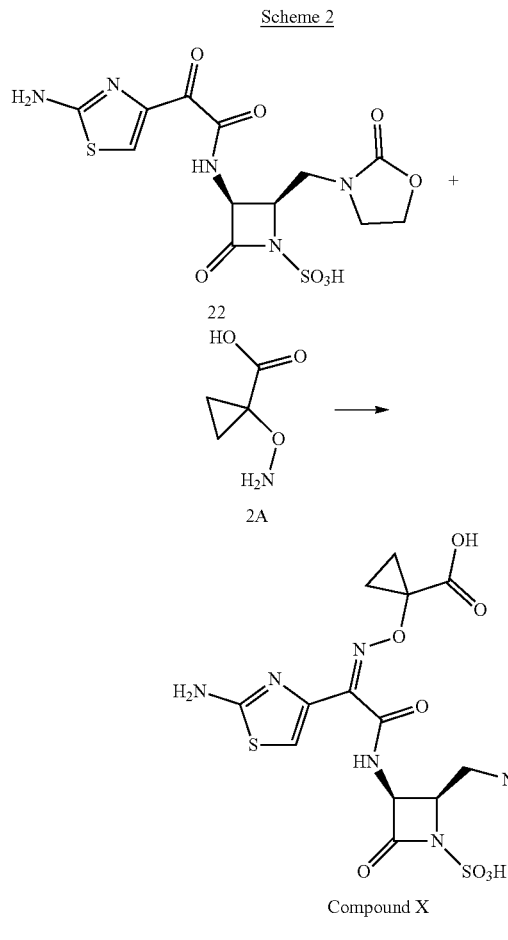

Compound X

The compound of formula 22 and the compound of formula (2A) are reacted together in a suitable solvent. The reaction is preferably performed at ambient temperature. Suitable solvents for the reaction can be any polar solvent. For example, the solvent is one or more solvents selected from tetrahydrofuran (THF), 1,2-dimethoxyethane, dimethylformamide (DMF), dimethylacetamide (DMAc), aromatic hydrocarbon, water, acetonitrile, alcohol solvents, N-formyl morpholine, dimethyl sulfoxide (DMSO), sulflane, or mixtures thereof. Preferably, the solvent is dimethylacetamide (DMAc).

The reaction of Scheme 2 is preferably performed, by reacting, in dimethylacetamide, the compound of formula 22 and the compound of formula 2A, at ambient temperature and stirring at ambient temperature for 3 days.

Thus, Compound X may be assembled without the need for nitrogen protecting groups to protect reactive nitrogen functionalities.

Preparation of Compound X From a Compound of Formula (I)

The compound of formula 22 can be prepared from a compound of formula (IB) and the compound of formula 21, according to Scheme 3.

In a further aspect, the present invention relates to a process for the preparation of compound 22, or a salt thereof, comprising the step of reacting a compound of formula (IB) with the compound of formula 21 in the presence of a solvent, with a base and a coupling agent, wherein $M^+$ is hydrogen or a pharmaceutically acceptable salt forming cation.

In a further aspect, the present invention relates to a process for the manufacture of Compound X, comprising the step of preparing a compound of formula 22, or a salt thereof, from a compound of formula (IB) and a compound of formula 21, and reacting the compound of formula 22, or a salt thereof, with the compound of formula (2A).

In yet a further aspect, the present invention relates to a process for the manufacture of Compound X, comprising the step of preparing a compound of formula 22, or a salt thereof, from a compound of formula (IB) and a compound of formula 21, and reacting the compound of formula 22, or a salt thereof, with the compound of formula (2A), wherein the compound of formula (IB) is prepared from a compound of formula (I), in particular, of formula (IA).

Scheme 3

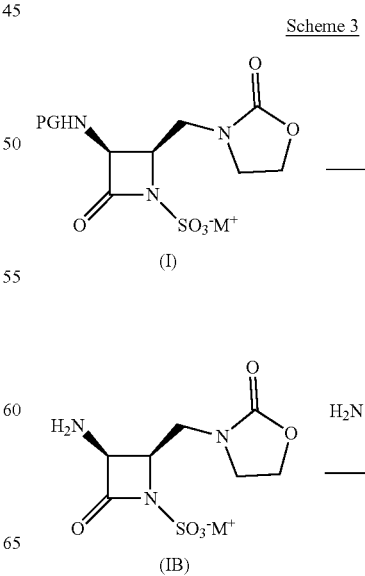

-continued

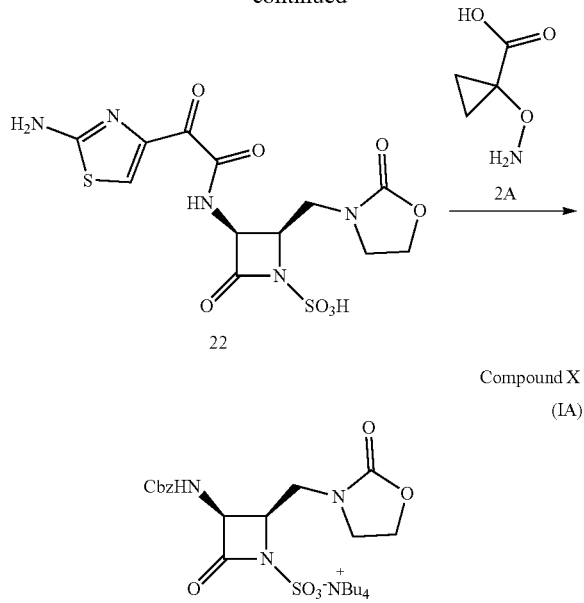

Thus, a further aspect of the present invention provides a process for the preparation of Compound X, from a compound of formula (IB), wherein the compound of formula (IB) is prepared from a compound of formula (I) comprising the step of deprotection of a compound of formula (I), wherein PG is a nitrogen protecting group, M⁺ is a pharmaceutically acceptable salt forming cation.

The compound of formula 21 can be prepared according to known literature procedures. The protecting group (PG) in a compound of formula (I) is removed under deprotection conditions. Depending on the protecting group employed, the skilled person would know how to remove the protecting group to obtain the free amine $NH_2$ group by reference to known procedures. These include reference to organic chemistry textbooks and literature procedures. The protecting group PG (for example, tert-butyloxycarbonyl (Boc), benzyloxycarbonyl (Cbz), methyloxycarbonyl, ethyloxycarbonyl, allyloxycarbonyl, phenyloxycarbonyl, formyl, acetyl or benzyl) can be removed under a condition selected from acid hydrolysis, base hydrolysis, reduction in the presence of a catalyst and hydrogen. Preferably the acid or base or catalytic reduction causes removal of the protecting group but at the same time does not cause chemical degradation of the compounds and intermediates. Acids commonly employed in removal of nitrogen protecting groups include, but are not limited to, HF.pyridine, HF.triethylamine ammonium fluoride, hexafluoroisopropanol, acetic acid, trifluoroacetic acid, hydrochloric acid, sulfuric acid, or a combination thereof.

Preferably, the protecting group in a compound of formula (I) is benzyloxycarbonyl (Cbz).

Preferably, the protecting group is removed by reduction in the presence of a catalyst and hydrogen.

The catalyst used to perform the reduction of compound of formula (I) is any catalyst that a skilled person would select from a general textbook. The catalyst can be selected from the group consisting of Raney nickel, Pt/C, Rh/C, Pd/Al$_2$O$_3$, Pd/CaCO$_3$, RhCl(PPh$_3$)$_3$, Lindlar catalyst, PtO$_2$, Pd/C, [Rh(cod)(PPh$_3$)$_2$]⁺, [Ir(cod)(PCy$_3$)(Py)]⁺, Pd(OH)$_2$, Pd(OAc)$_2$, Pd$_2$(dba)$_3$, Zn, Fe, Sm, NiCl$_2$, Ni(OAc)$_2$, CoCl$_2$, ZrCl$_4$, TiCl$_3$. The catalyst can be present in a range from about 0.005 mol % to about 20.0 mol %. Typically, the catalyst can be present in an amount below 10.0 mol % (to about 0.005 mol %).

The reduction may be performed in a solvent such as an alcohol based solution. The alcohol based solution can comprise or consist of $C_1$ to $C_{10}$ alcohols (e.g. methanol, ethanol, propanol, 2-propanol and butanol) or mixtures thereof.

The deprotection of a compound of formula (I), as defined by Scheme 3, is preferably carried out at elevated pressure, preferably between 1 bar and 10 bar, particularly between 1 and 2 bar. Reduction of the compound of formula (I), is preferably performed by stirring the reaction mixture for 24 hours at or near ambient temperature, with 10 mol % of Pd/C under a hydrogen atmosphere (1-2 bar) in the presence of methanol, to produce a compound of formula (IB). The reduction is preferably carried out with the protecting group PG being selected from benzyloxycarbonyl (Cbz), fluorenylmethyloxycarbonyl (Fmoc), allyloxycarbonyl, and benzyl.

Examples of the group represented by M⁺ for forming a salt of a compound of formula 21 include the inorganic base salts, ammonium salts, organic base salts, basic amino acid salts. Inorganic bases that can form the inorganic base salts include alkali metals (e.g., sodium, potassium, lithium) and alkaline earth metals (e.g., calcium, magnesium); organic bases that can form the organic base salts include amines such as cyclohexylamine, benzylamine, octylamine, ethanolamine, diethanolamine, diethylamine, triethylamine, morpholine, pyrrolidine, piperidine, N-ethylpiperidine, N-methylmorpholine; basic amino acids that can form the basic amino acid salts include lysine, arginine, ornithine and histidine. Preferably, the group represented by M⁺ for forming a suitable salt of a compound of formula 21 is an aminium ion, e.g. a tri-N—($C_{1-4}$)alkyl ammonium cation. Preferably, the group is the triethylammonium cation (Et$_3$NH⁺).

The compound of formula (IB) and the compound of formula 21 are reacted together in a suitable solvent, in the presence of a a coupling agent and optionally also a base. The reaction is preferably performed at ambient temperature. Suitable solvents for the reaction can be any polar solvent. For example, the solvent is one or more solvents selected from tetrahydrofuran (THF), 1,2-dimethoxyethane, dimethylformamide (DMF), dimethylacetamide (DMAc), aromatic hydrocarbon, acetonitrile, 2-methyltetrahydrofuran (Me-THF), water, or mixtures thereof. Preferably, the solvent is dimethylformamide (DMF).

The coupling agent should be known to a person of skill in the art or can be determined. E.g. the coupling agent may be one or more coupling agents selected from N,N'-carbonyldiimidazole, ethyl chloroformate, ethoxyl-ethoxycarbonyl-1,2-dihydroquinoline (EEDQ), isobutyl chloroformate, isopropenyl chloroformate, trimethylacetyl chloride, 2,4,6-trichlorobenzoyl chloride, isobutyl chloroformate, 4-nitrophenyl chloroformate, cyanuric chloride, oxalyl chloride, dimethylformamide/POCl$_3$ (Vilsmeier's reagent), N-Ethyl-N-(3-dimethylaminopropyl)carbodiimide (EDC), organophosphorus reagents, 2-Chloro-4,6-dimethoxy-1,3,5-triazine (CDMT), 2-Bromo-1-ethyl-pyridinium tetrafluoroborate (BEP), Tri(dimethylamino)benzotriazol-1-yloxyphosphonium hexafluorophosphate (BOP), 7-Azabenzotriazol-1-yloxytris(dimethylamino)phosphonium hexafluorophosphate CDMT. Preferably, the coupling agent is an organophosphorus reagent, Vilsmeier's reagent, CDMT. Preferably, the coupling agent is an organophosphorus reagent, most preferably diphenylphosphinic chloride.

The base when used to perform the reaction of Scheme 3 should be known to a person of skill in the art or can be determined. The base can be for example sodium carbonate ($Na_2CO_3$), potassium carbonate ($K_2CO_3$), cesium carbonate ($Cs_2CO_3$), potassium phosphate tribasic ($K_3PO_4$), sodium phosphate tribasic ($Na_3PO_4$), N,N-diisopropylethylamine (DIPEA), triethylamine ($Et_3N$), sodium acetate (NaOAc), potassium acetate (KOAc), N-methylmorpholine (NMM) and 4-dimethylaminopyridine (DMAP), or mixtures thereof. The preferred base in this process is one or more bases selected from $K_2CO_3$, $Cs_2CO_3$, $K_3PO_4$, DIPEA, NMM, DMAP, and $Et_3N$. Most preferably, the reaction is performed in the presence of triethylamine.

The synthesis of compound 22 of Scheme 3 is preferably performed, by combining the compound of formula 21 and diphenylphosphinic chloride in a suitable solvent such as DMF, and allowing them to react at a suitable temperature, for example about −20° C., with agitation for at least about 30 min. This mixture is combined with a compound of formula (IB) and a suitable base such as triethylamine. The reaction mixture is stirred at a suitable temperature, e.g., ambient temperature, for about 20 h or until deemed complete.

Preparation of a Compound of Formula IV

This section relates to a process for the manufacture of a compound of formula (IV), wherein a compound of formula (VII), is reacted by a dynamic kinetic resolution (DKR) under asymmetric reduction conditions to obtain a compound of formula (VIIc), or a salt thereof, as defined herein. Accordingly, an aspect of the present invention relates to a process for the preparation of a compound of formula (IV)

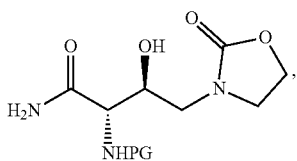

(IV)

wherein PG is a nitrogen protecting group, comprising the step of reducing a compound of formula (VII), under asymmetric reduction conditions, to produce the compound of formula (VIM, or a salt thereof, enriched in one enantiomer and diastereomer, wherein PG is a nitrogen protecting group, R is branched or linear $C_1$-$C_7$ alkyl, benzyl, $C_1$-$C_4$-alkoxy substituted benzyl, and X is selected from the group consisting of halide, carboxylate, and sulfonate, as defined in Scheme 4.

Scheme 4

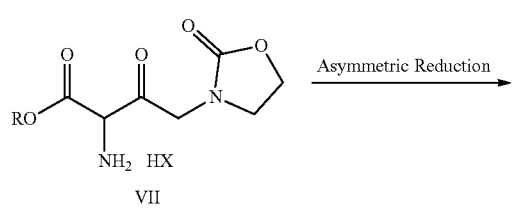

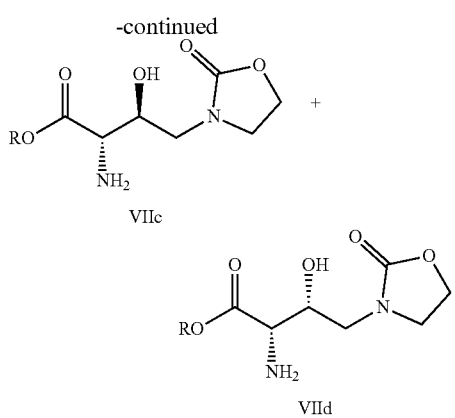

Dynamic kinetic resolutions (DKR) are described in "Enantioselective Synthesis: The Optimum Solution", Partridge, J. J. and Bray, B. L. in Process Chemistry in the Pharmaceutical Industry, (Gadamasetti, K. G., Ed.) Marcel Dekker, New York, N.Y., 1999, pp. 314-315.

The asymmetric reduction conditions of scheme 4 may employ a chiral transition metal catalyst in the presence of hydrogen.

The efficiency of the enantio- and diastereoselective synthesis of the compound of formula (VIIc) is highly influenced by substrate structures and reaction conditions. This includes choice of solvent, temperature and pressure of hydrogen. Hence, the reaction conditions have to be chosen very carefully for the transformation of the compound of formula (VII) to the compound of formula (VIIc), outlined in Scheme 4.

The stereoselective hydrogenation of functionalised ketones by BINAP-Ruthenium(II) complexes and dynamic kinetic resolution, is described in Noyori, et al., *J. Am. Chem. Soc.* 1993, 115, 144-152. The chiral transition metal catalyst can be, for example, a Ru(II) ligand complex of the formula L*$RuX_2$, wherein $X_2$ is a halide, preferably chloride or bromide, L* is a chiral ligand and can have (R) or (S) stereochemical configuration, depending on the desired stereochemical confirguration of the resulting product. The Ru(II) complex of the formula L*$RuX_2$ can also be synthesised in situ, for example, by ligand exchange of a ruthenium complex of formula $RuX_2$[ solvent] or [$RuX_2$(solvent)]$_2$, wherein the solvent is, for example, an exchangeable ligand solvent, for example, benzene, p-cymene. The ligand can be, for example, but not limited to, BINAP, CHIRAPHOS, SYNPHOS, BnDPAE, TsDPEN, $C_6F_5SO_2$DPEN, $CF_3SO_2$DPEN, N-trifluoromethanesulfonyl-1,2-cyclohexanediamine. The skilled person will readily understand what stereochemical configuration of the chiral ligand is needed, depending on the desired stereochemical confirguration of the resulting product. Preferably, for the reaction to provide Compound (VIIc), the ligand is (S)—BINAP. Preferably, the chiral transition metal catalyst is (S)—BINAPRuCl$_2$.

The inventors of the present reaction have found that the dynamic kinetic resolution and asymmetric hydrogenation in the presence of (S)—BINAPRuCl$_2$ result in the production of an amino alcohol compound of formula (VIIc), in high enantioselectivity and diastereoselectivity, thus contributing to the overall efficiency of the process and high optical purity of the intermediate compound of formula (VIIc) of the present invention.

The asymmetric hydrogenation of a compound of formula (VII) in the presence of (S)—BINAPRuCl$_2$ proceeds with high chemical conversion and with a de of the desired diastereomer VIIIc:VIId of 97.6% and an ee of greater than 99.5%.

Thus, the production of an amino alcohol compound of formula (VIIc), in high enantioselectivity and diastereoselectivity, contributes to the overall efficiency of the process and provides high optical purity of the intermediate compound of formula (VIIc), while deriving the desired absolute stereochemistry from a re-usable chiral catalyst ligand rather than requiring use of an enantio-pure starting material.

Thus, in another aspect, the present invention provides a compound of formula (VIIc) which is a very useful intermediate in the manufacture of Compound X.

In a preferred aspect, the asymmetric reduction, as defined in Scheme 4, employs (S)—BINAPRuCl$_2$ and hydrogen, to obtain a compound of formula (VIIc).

The reaction mixture is normally heated. Suitable solvents that can be employed in the reaction are, for example, dichloromethane, alcohol solvents, or mixtures thereof.

The reaction of Scheme 4 is preferably performed by reacting, in an autoclave, a racemic compound of formula (VII), in dichloromethane with (S)—BINAPRuCl$_2$ in the presence of hydrogen (2.1±0.1 MPa) at 40±5° C. for 24 h.

In an embodiment the present invention provides a process for the preparation of a compound of formula (IV) comprising the step of reducing a compound of formula (VII) under asymmetric reduction conditions to produce the compound of formula (VIIc), or a salt thereof.

A further aspect of the present invention provides a process for the preparation of a compound of formula (IV), summarized in Scheme 5, comprising the step of reducing a compound of formula (VII) under asymmetric reduction conditions to produce the compound of formula (VIIc), or a salt thereof, and further comprising the steps of protecting the NH$_2$ group in a compound of formula (VIM, to produce a compound of formula (Vile), followed by reacting the compound of formula (Vile) with a source of ammonia to obtain a compound of formula (IV).

protecting group, as defined herein, in a solvent in the presence of a base. Suitable reagents and conditions for this protection step are well known in the art. The reaction is preferably performed at ambient temperature. Suitable solvents that can be employed in the reaction are, for example, water, toluene, alcohol solvents, or mixtures thereof. Suitable bases that can be employed in the reaction are, for example, metal hydrogen carbonates, metal carbonates, and metal hydroxides.

The reaction of step (ii), as defined by Scheme 5, is preferably performed by reacting a compound of formula (VIIc), in a mixture of toluene and water, at a temperature of 0-5° C., with benzyl chloroformate (CbzCl) in the presence of a base such as NaHCO$_3$. The resulting reaction mixture is preferably stirred at 25-35° C. for 18-25 h or until the reaction is substantially complete.

In a further step, the compound of formula (VIIe), is reacted with an ammonia source to produce the compound of formula (IV). The reaction is preferably carried out in a solvent. The reaction is preferably heated. Suitable solvents for the reaction can be any polar solvents. For example, the solvent is one or more solvents selected from tetrahydrofuran (THF), alcohol solvents, methyl tertbutylether (MTBE), 2-methyltetrahydrofuran, 1,2-dimethoxyethane, aromatic hydrocarbon or mixtures thereof. The ammonia source used to perform the reaction as defined in Scheme 5 may be any ammonia source that is known to a person skilled in the art. Suitable ammonia sources for the reaction include, but are not limited to, ammonia (NH$_3$), ammonium bicarbonate (NH$_4$HCO$_3$), ammonium chloride (NH$_4$Cl), magnesium nitride (Mg$_3$N$_2$). The ammonia is optionally gaseous, concentrated liquid ammonia, gaseous ammonia mixed with one or more solvents of step (iii), for example, ammonia mixed with tetrahydrofuran.

The reaction of step (iii), as defined by Scheme 5, is preferably performed by combining, in a pressurizable container such as an autoclave, a compound of formula (VIIe) in a suitable solvent such as tetrahydrofuran, preferably at a temperature between −75 and −65° C., with ammonia, for example by bubbling gaseous ammonia in the reaction mixture for about 4 h or until sufficient ammonia has been added. The resulting reaction mixture is preferably agitated at ambient temperature for 16-20 h or until the reaction is substantially complete.

Preparation of Compound of Formula (I)

In a further aspect, the present invention relates to a process for the manufacture of a compound of formula (I), as defined in Scheme 6, preferably of formula (IA), wherein the hydroxyl group of a compound of formula (IV), is transformed into a leaving group (OLG), to produce a compound of formula (III), followed by sulfonation of a compound of formula (III) with a halosulfonic acid, followed by reacting with a pharmaceutically acceptable salt forming cation reagent, to produce a compound of formula (II). A stereospecific cyclisation of a compound of formula (II) is carried out by reacting a compound of formula (II) with a base to obtain a compound of formula (I), as outlined in Scheme 6.

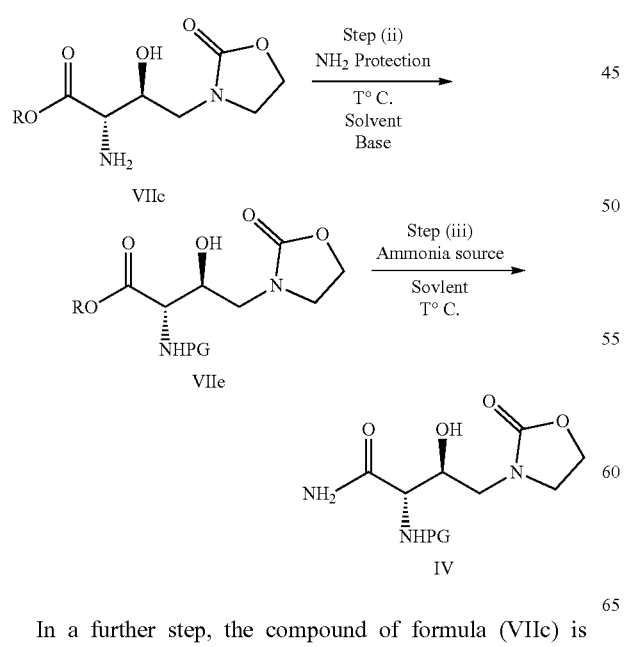

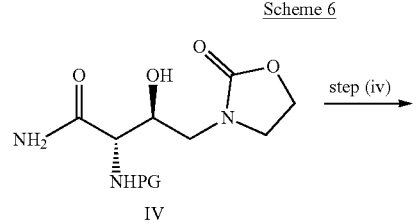

In a further step, the compound of formula (VIIc) is reacted with a reagent, suitable for introducing a nitrogen

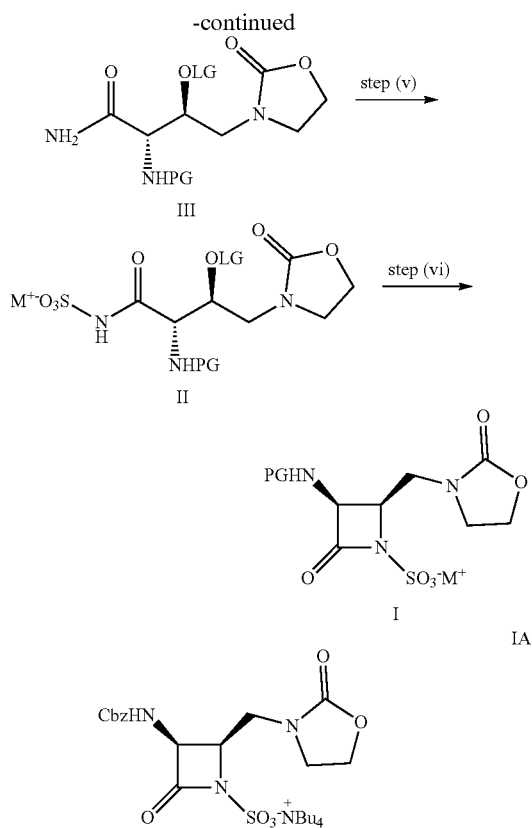

Accordingly, in one aspect, the present invention provides a process for preparing a compound of formula (I), preferably wherein the compound of formula (I) is of formula (IA), comprising the steps of (iv) converting a compound of formula (IV) to a compound of formula (III), wherein LG is SO₂T, wherein T is selected from C₄F₉, CH, F, C₆H₄CH₃, CH₅, C₆H₆, and PG is as defined herein, followed by, (v) contacting a compound of formula (III), in a solvent with a base and a sulfonylating agent such as a halosulfonic acid, preferably chlorosulfonic acid, and a salt forming reagent, to produce a compound of formula (II), wherein M⁺ is hydrogen or a salt forming cation, LG and PG are as defined herein, followed by, (vi) reacting a compound of formula (II) in a solvent with a base, preferably under flow preparation conditions, to produce a compound of formula (I).

The OH group in a compound of formula (IV), is converted by methods known in the art into a suitable leaving group (OLG), wherein LG is selected from —SO₂T, wherein T is selected from C₄F₉, CF₃, F, C₆H₄CH₃, CHs, C₆H₆. A leaving group as disclosed herein is a molecular fragment or stable species that can be detached from a molecule in a bond-breaking step. The leaving group, in accordance with the present invention, is not particularly limited and should be known to a person of skill in the art or can be determined. The ability of a leaving group to depart is correlated with the pKa, of the conjugate acid, with lower pKa, being associated with better leaving group ability. Examples of leaving group include, but are not limited to, sulfonate, water, alcohols, inorganic esters such as nitrate or phosphate, carboxylate, phenoxide, alkoxide. Examples of sulfonates include, without limitation, nonaflate (OLG=—OSO₂C₄F₉), triflate (OLG=—OSO₂CF₃), fluorosulfonate (OLG=—OSO₂F), tosylate (OLG=—OSO₂C₆H₄CH₃), mesylate (OLG=—OSO₂CH₃) or besylate (OLG=OSO₂C₆H₆). The process for the conversion of a hydroxyl group to a leaving group (OLG) is known to a person skilled in the art.

In one aspect of the present invention, the hydroxyl group of a compound of formula (IV) is converted into a leaving group, by reacting a compound of formula (IV), in a solvent with a base and a sulfonyl halide, preferably a sulfonyl chloride, of formula (A),

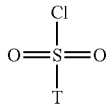

(A)

wherein T is selected from C₄F₉, CF₃, F, C₆H₄CH₃, CH₃, C₆H₆.

In a preferred aspect, the hydroxyl group of a compound of formula (IV) is converted into a mesylate group.

As outlined in step (iv) of Scheme 4, the compound of formula (IV) is reacted with a reagent of formula (A), in a solvent in the presence of a base. The reaction is preferably performed at −5-0° C. Suitable solvents for the reaction can be any polar aprotic solvent. For example, the solvent is one or more solvents selected from tetrahydrofuran (THF), 2-methyl THF, 1,2-dimethoxyethane, dimethylformamide (DMF), dimethylacetamide (DMAc), aromatic hydrocarbon, dichloromethane (DCM), 1,2-dichloroethane (DCE), or mixtures thereof. The base suitable to perform the reaction of step (iv) of Scheme 4 should be known to a person of skill in the art or can be determined. A suitable base that can be employed in the reaction is an amine base. For example, the amine base is selected from, but not limited to, optionally substituted trialkylamines or optionally substituted aromatic amines, or mixtures thereof. Suitable amines include, for example, triethylamine, tri-n-propylamine, tri-n-butylamine. N,N-diisopropylethylamine, N,N-dimethylcyclohexylamine, pyridines (including methyl substituted pyridine (2-, 3-, or 4-picoline, 2,6-lutidine)), pyrazines, DMAP, pyrroles, purines, and pyrimidines. Preferably, the base is triethylamine.

The reaction of step (iv), as defined by Scheme 4, is preferably performed by reacting a compound of formula (IV), in 1,2-dimethoxyethane, with a sulfonyl halide, preferably chloride, preferably methanesulfonyl chloride, at a temperature between −5-0° C., followed by addition of triethylamine. The resulting reaction mixture is optionally stirred at about −5-0° C. until the reaction is substantially complete.

In a further step, the amide group of a compound of formula (III) is activated, by conversion into a sulfamate group, to produce a compound of formula (II), which undergoes subsequent cyclisation, in the presence of a base, to produce the beta-lactam compound of formula (I). This stereospecific cyclization of an activated amide, with a leaving group, is described in Epstein, et al., *J. Org. Chem.* 1982, 47, 176-178.

As outlined in step (v) of Scheme 6, the compound of formula (III) is reacted with a sulfonating agent, and a suitable reagent serving as a salt forming cation, i.e. a source of M⁺. The sulfonating agent for step (v) of Scheme 4 is any sulfonating agent that would be known to the skilled person in the art or can be determined. Suitable reagents include, but are not limited to, sulfur trioxide, oleum, halosulfonic acids and sulfur trioxide addition compounds. Among the applicable addition compounds of sulfur trioxide are included the complexes of sulfur trioxide with complexing agents such as pyridine, methyl substituted pyridine (2-, 3-, or 4-picoline, 2,6-lutidine), trialkylamines, dimethylformamide, and ethers. Preferably, the sulfonating agent is selected from halosulfonic acid, and addition compounds of sulfur trioxide, as defined herein. Preferably, addition compounds of sulfur trioxide are synthesised in situ. More preferably, the sulfonating agent of step (v) is an addition compound of sulfur trioxide. Most preferably, the sulfonating agent is the complex of sulfur trioxide with 2-picoline, which may be formed by combining $SO_3$ or chlorosulfonic acid with 2-picoline.

Examples of the group for forming a suitable salt represented by $M^+$ in a compound of formula (II), (I) or (IB) include the inorganic base salts, tetra-substituted ammonium salts, organic base salts, basic amino acid salts. Inorganic bases that can form the inorganic base salts include alkali metals (e.g., sodium, potassium, lithium) and alkaline earth metals (e.g., calcium, magnesium); organic bases that can form the organic base salts include cyclohexylamine, benzylamine, octylamine, ethanolamine, diethanolamine, diethylamine, triethylamine, morpholine, pyrrolidine, piperidine, and N-ethylpiperidine, N-methylmorpholine; basic amino acids that can form the basic amino acid salts include lysine, arginine, omithine and histidine. Preferably, the group for forming a salt represented by $M^+$ is a tetra-alkyl ammonium salt. Preferably, the group is a tetrabutylammonium cation ($NBu_4^+$).

The reaction as outlined in step (v) of Scheme 6, the compound of formula (III) is reacted in a solvent, at a temperature of 0-5° C., with a sulfonating agent, as defined herein. The reaction is preferably heated. Addition of a suitable salt forming reagent, as a source of $M^+$, as defined herein, is preferably added, in a solvent, at 10-20° C. Suitable solvents for the reaction can be any polar solvents. For example, the solvent is one or more solvents selected from tetrahydrofuran (THF), 1,2-dimethoxyethane, dichloromethane, dimethylformamide (DMF), dimethyl acetamide (DMAC), 4-formyl morpholine, water or mixtures thereof. The sulfonating agent is preferably prepared in situ, by reacting a halosulfonic acid, preferably chlorosulfonic acid, with an amine base, preferably 2-picoline, in a solvent, preferably dimethylformamide, at a temperature of 0-5° C. Preferably, the solvent for the in situ formation of the sulfonating agent is DMF. Preferably, the solvent for the addition of the reagent serving as a pharmaceutically acceptable salt forming cation, i.e. a source of $M^+$, is a mixture of dichloromethane and water, preferably in the ratio of 1:1 (v/v).

The reaction of step (v), as defined by Scheme 6, is preferably performed by reacting, in DMF, 2-picoline and chlorosulfonic acid at a temperature of about 5° C. The reaction mixture is stirred at 20° C., followed by addition of a compound of formula (III). The reaction mixture is heated to a suitable temperature to promote the reaction, e.g. 30-45° C., preferably the reaction mixture is heated at 30-45° C. for 15-20 h, or until conversion of starting material is substantially complete. A solution of tetrabutylammonium hydrogensulfate in a mixture of dichloromethane and water (1:1) (v/v) is added at 5° C., to produce a compound of formula (II).

The reaction outlined in step (vi), as defined by Scheme 6, is effected with a base. Suitable bases that can be employed in the reaction are, for example, alkali metal carbonates, bicarbonates, or hydroxides, quaternary ammonium carbonate, bicarbonate, or hydroxide; and tertiary amines. Preferably, the base is an alkali metal bicarbonate. More preferably, the base is potassium bicarbonate ($KHCO_3$).

Suitable solvents for the reaction can be any polar solvents. For example, the solvent is one or more solvents selected from tetrahydrofuran (THF), 1,2-dimethoxyethane, dichloromethane, dimethylformamide (DMF), dimethyl acetamide (DMAC), water or mixtures thereof.

Due to the structural complexity of the compound of formula (II), the inventors of the present invention have developed a novel flow procedure to enable such transformation of a compound of formula (II) to a compound of formula (I) in high yield. The flow preparation conditions include, for example, using a pump, two injection loops (one for each of the compounds of the formula (II) and the base), a cross-mixer, followed by a reactor coil (tube coil) that is heated, for example by being placed in an oil bath, at 90–110° C., followed by a back-pressure regulator at pressure 6-20 bar.

The reaction as outlined in step (vi), as defined by Scheme 6, is preferably performed under flow preparation conditions. More preferably, the reaction as outlined in step (vi), as defined by Scheme 6, is performed under flow preparation conditions using an alkali metal bicarbonate base. Most preferably, the reaction is performed under flow preparation conditions using potassium bicarbonate.

The reaction of step (vi), as defined by Scheme 6, is preferably performed by reacting, in dichloromethane, under flow preparation conditions, a compound of formula (II) with a solution of $KHCO_3$ in water and heated to about 100° C.

Complete Sequence of the Preparation of a Compound of Formula (I)

In a further aspect, the compound of formula (I), preferably of formula (IA), is obtained by a reaction sequence as outlined in Scheme 7,

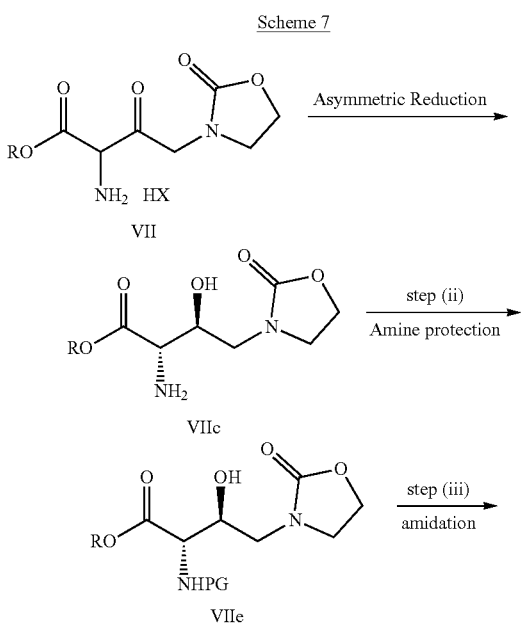

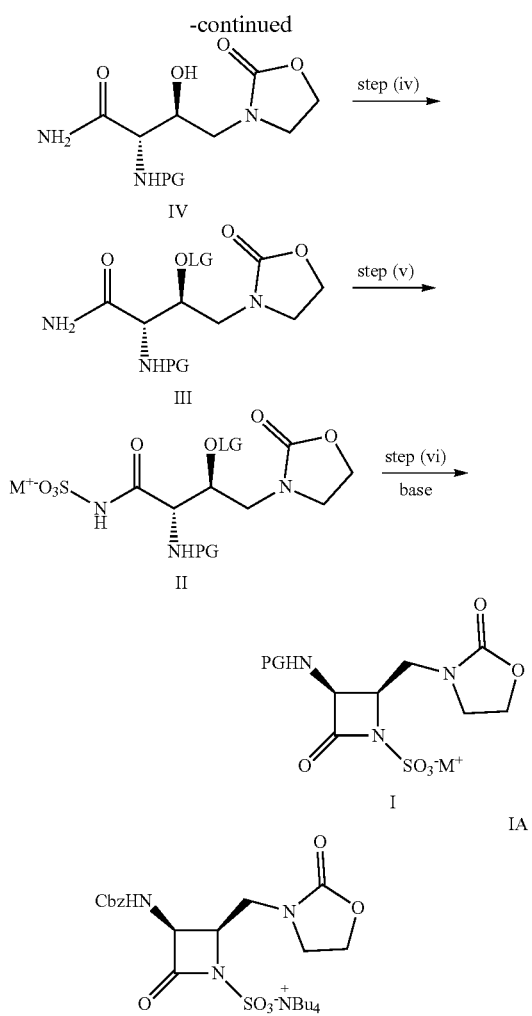

wherein PG is a nitrogen protecting group, as defined herein, R is selected from branched or linear $C_1$-$C_7$ alkyl, benzyl, and $C_1$-$C_4$-alkoxy substituted benzyl, X is selected from the group consisting of halide, carboxylate, and sulfonate, LG is $SO_2T$, wherein T is selected from $C_4F_9$, $CF_3$, F, $C_6H_4CH_3$, $CH_3$, and $C_6H_6$, and $M^+$ is hydrogen or a suitable salt forming cation.

As outlined in Scheme 7, in the initial three-step reaction sequence, a compound of formula (IV) is obtained by a dynamic kinetic resolution of a compound of formula (VII), under asymmetric reduction conditions, comprising reacting a compound of formula (VII) with a catalyst and hydrogen, wherein the catalyst is a Ru(II) complex, preferably (S)—BINAPRuCl$_2$. The obtained compound of formula (VIIc), enriched in one enantiomer and diastereomer, is then protected with a nitrogen protecting group, as defined herein, to produce a compound of formula (VIIe). Preferably, the nitrogen protecting group is benzyloxycarbonyl (Cbz). Then, the obtained compound of formula (VIIe) is reacted with an ammonia source, preferably ammonia, to produce a compound of formula (IV). The compound of formula (IV) is further reacted with a reagent, suitable to convert the hydroxyl into a leaving group, as defined herein, in a solvent in the presence of a base. Preferably, the reagent is a sulfonyl halide, preferably chloride, preferably methanesulfonyl chloride. Preferably, the solvent is one or more polar aprotic solvents. For example, the solvent is one or more solvents selected from tetrahydrofuran (THF), 2-methyl THF, 1,2-dimethoxyethane, dimethylformamide (DMF), dimethylacetamide (DMAc), aromatic hydrocarbon solvent, dichloromethane (DCM). 1,2-dichloroethane (DCE), or mixtures thereof. More preferably, the solvent is selected from tetrahydrofuran (THF), 1,2-dimethoxyethane or a mixture thereof. Preferably, the base is an amine base. For example, the amine base is selected from, but not limited to, optionally substituted trialkylamines or optionally substituted pyridine, or optionally substituted aromatic amines, or mixtures thereof. Suitable amines include, for example, triethylamine, tri-n-propylamine, tri-n-butylamine. N,N-diisopropylethylamine, N,N-dimethylcyclohexylamine, pyridines (including methyl substituted pyridine (2-, 3-, or 4-picoline, 2,6-lutidine)), pyrazines, pyrroles, purines, pyrimidines. Preferably, the base is triethylamine. The obtained compound of formula (III) is then reacted with a sulfonating agent, to produce the sulfamate group in a compound of formula (II), followed by addition of a suitable reagent providing a suitable salt forming cation $M^+$. Preferably, the sulfonating reagent is formed in situ, by reacting a halosulfonic acid, preferably chlorosulfonic acid, with an amine or pyridine base, preferably 2-picoline, in a solvent, to produce the 2-picoline●$SO_3$ complex. Addition of a suitable reagent serving as a suitable salt-forming cation $M^+$, as defined herein, is preferably performed in a solvent. The solvent is one or more polar solvents selected from tetrahydrofuran (THF), 1,2-dimethoxyethane, dichloromethane, dimethylformamide (DMF), dimethyl acetamide (DMAC), N-formyl morpholine, water or mixtures thereof. Preferably, the solvent for the in situ formation of the sulfonating agent is DMF. Preferably, the solvent for the addition of the reagent serving as a salt forming cation $M^+$ is a mixture of dichloromethane and water, preferably in the ratio of 1:1 (v/v). Lastly, the compound of formula (II) is further reacted, in a base induced cyclisation to obtain a compound of formula (I), preferably of formula (IA).

Alternative Follow on Reaction of a Compound of Formula (I) to Produce Compound X In another aspect of the invention, the products of the process(es) of the present invention can be used in the synthesis of Compound X or a salt thereof, or a solvate including hydrate thereof, as described herein. In a preferred aspect of the present invention, the compound of formula (I), preferably of formula (IA), is further reacted to obtain Compound X.

The compound of formula (I), preferably of formula (IA), can undergo a deprotection reaction, to remove the nitrogen protecting group. A similar procedure is described, for e.g., in PCT/US2015/022011 and PCT/CN2016/099482. The resulting compound of formula (IB) is then further reacted with a compound of formula (3), to produce a compound of formula (4), followed by deprotection of the ester group, to obtain Compound X, as outlined in Scheme 8.

Scheme 8

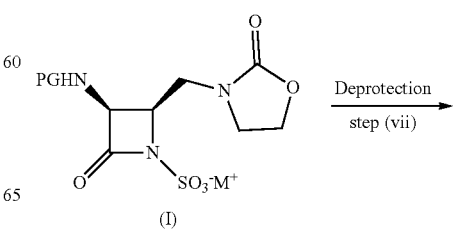

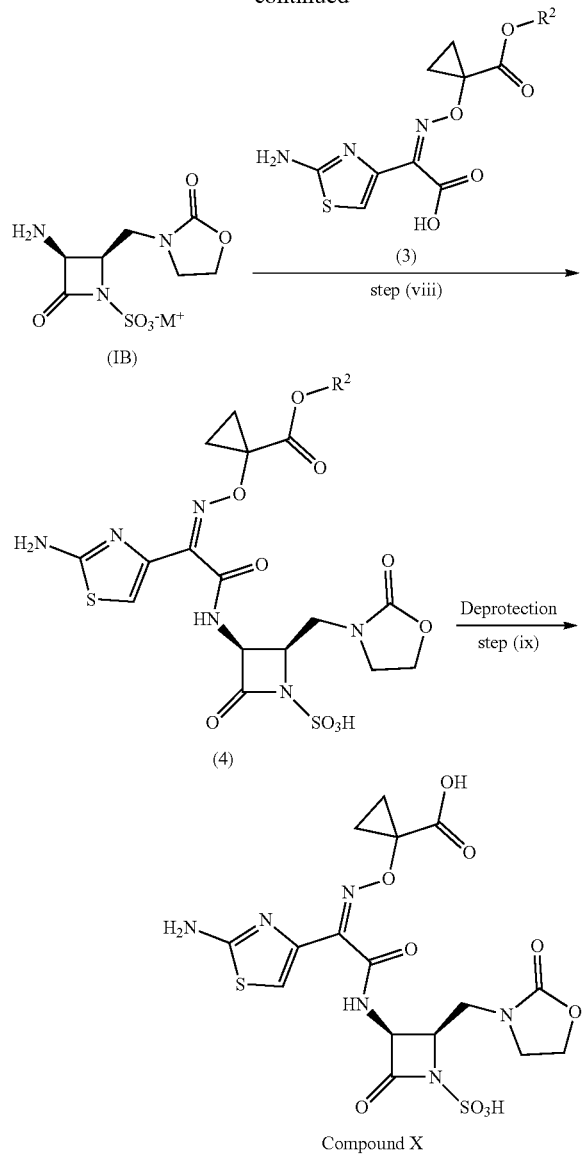

Accordingly, in a further aspect, the subject of the present invention is a process for preparing Compound X, or a salt thereof, or a solvate including hydrate thereof, as described herein, from a compound of formula (I), preferably of formula (IA), comprising the steps of, (vii) removal of the PG group in a compound of formula (I), wherein the PG group is as defined herein, under a condition selected from acid hydrolysis, reduction in the presence of a catalyst and hydrogen, wherein the catalyst is selected from the group consisting of Raney nickel, Pt/C, Rh/C, Pd/Al$_2$O$_3$, Pd/CaCO$_3$, RhCl(PPh$_3$)$_3$, Lindlar catalyst, PtO$_2$, Pd/C, [Rh(cod)(PPh$_3$)$_2$]$^+$, [Ir(cod)(PCy$_3$)(Py)]$^+$, Pd(OH)$_2$, Pd(OAc)$_2$, Pd$_2$(dba)$_3$, Zn, Fe, Sm, NiCl$_2$, Ni(OAc)$_2$, CoCl$_2$, ZrCl$_4$, TiCl$_3$, to obtain a compound of formula (IB), wherein M$^+$ is as defined herein, followed by, (viii) reacting a compound of formula (IB) with a compound of formula (3), in a solvent, with a base and a coupling agent, to produce a compound of formula (4), wherein R$_2$ is selected from branched or linear C$_1$-C$_7$-alkyl, benzyl, C$_1$-C$_4$-alkoxy substituted benzyl, CH(aryl)$_2$, followed by, (ix) deprotection of the ester group R$^2$ in a compound of formula (4), wherein the deprotection is carried out under a condition selected from addition of acid, base, acid and hydrosilane, and reduction in the presence of a catalyst and hydrogen.

Preferably the deprotection is carried out by contacting the compound of formula (4) with a suitable acid, wherein the acid is selected from acetic acid, trifluoroacetic acid, bromoacetic acid, chloroacetic acid, formic acid, methanesulfonic acid, hydrochloric acid, sulfuric acid, to obtain Compound X. Preferably, the acid is trifluoroacetic acid.

The protecting group (PG) in a compound of formula (I) is removed under deprotection conditions. Depending on the protecting group employed, the skilled person would know how to remove the protecting group to obtain the free amine NH$_2$ group by reference to known procedures. These include reference to organic chemistry textbooks and literature procedures. The protecting group PG (for example, teabutyloxycarbonyl (Boc), benzyloxycarbonyl (Cbz), methyloxycarbonyl, ethyloxycarbonyl, allyloxycarbonyl, phenyloxycarbonyl, formyl, acetyl or benzyl) can be removed under a condition selected from acid hydrolysis, base hydrolysis, reduction in the presence of a catalyst and hydrogen. Preferably the acid or base or catalytic reduction causes removal of the protecting group but at the same time does not cause chemical degradation of the compounds and intermediates. Acids commonly employed in removal of nitrogen protecting groups include, but are not limited to, HF.pyridine, HF.triethylamine ammonium fluoride, hexafluoroisopropanol, acetic acid, trifluoroacetic acid, hydrochloric acid, sulfuric acid, or a combination thereof.

Preferably, the protecting group in a compound of formula (I) is benzyloxycarbonyl (Cbz).

Preferably, the protecting group is removed by reduction in the presence of a catalyst and hydrogen.

The catalyst used to perform the reduction of compound of formula (I) is any catalyst that a skilled person would select from a general textbook. The catalyst can be selected from the group consisting of Raney nickel, Pt/C, Rh/C, Pd/Al$_2$O$_3$, Pd/CaCO$_3$, RhCl(PPh$_3$)$_3$, Lindlar catalyst, PtO$_2$, Pd/C, [Rh(cod)(PPh$_3$)$_2$]$^+$, [Ir(cod)(PCy$_3$)(Py)]$^+$, Pd(OH)$_2$, Pd(OAc)$_2$, Pd$_2$(dba)$_3$, Zn, Fe, Sm, NiCl$_2$, Ni(OAc)$_2$, CoCl$_2$, ZrCl$_4$, and TiCl$_3$. The catalyst can be present in a range from about 0.005 mol % to about 20.0 mol %. Typically, the catalyst can be present in an amount below 10.0 mol % (down to about 0.005 mol %).

The reduction may be performed in a solvent such as an alcohol based solution. The alcohol based solution can comprise or consist of C$_1$ to C$_{10}$ alcohols (e.g. methanol, ethanol, propanol, 2-propanol and butanol) or mixtures thereof.

The reaction of step (vii), as defined by Scheme 8, is preferably carried out under the condition of reduction in the presence of a catalyst and hydrogen, at elevated pressure, preferably between 1 bar and 10 bar, particularly between 1 and 2 bar. Reductive deprotection of the compound of formula (I), is preferably performed by stirring the reaction mixture for 24 hours at room temperature, with 10 mol % of Pd/C under a hydrogen atmosphere (1-2 bar) in the presence of methanol, to produce a compound of formula (IB). The reduction is preferably carried out with the protecting group PG being selected from benzyloxycarbonyl (Cbz), fluorenylmethyloxycarbonyl (Fmoc), allyloxycarbonyl, or benzyl.

Thus in a further aspect, the present invention relates to a process for preparing a compound of formula (IB), or a salt thereof.

In a further step, the compound of formula (IB) is reacted in a solvent and optionally in the presence of base, with a compound of formula (3) and a coupling agent, to produce the compound of formula (4), wherein $R^2$ is selected from $C_1$-$C_7$-alkyl, benzyl, $C_1$-$C_4$-alkoxy substituted benzyl, and CH(aryl)$_2$; for example, —CH(phenyl)$_2$.

The reaction can be performed at ambient temperature. Suitable solvents used for the reaction can be any polar solvents. For example, the solvent is one or more solvent(s) selected from tetrahydrofuran (THF), dimethylformamide (DMF), dimethylacetamide (DMAc), N-methyl-2-pyrrolidone (NMP), N-butyl-2-pyrrolidone, dichloromethane (DCM), acetonitrile, ethanol, methanol, ethyl acetate, n-propanol, 2-propanol, n-butanol, 2-butanol, tert-butanol, and 2-methyl-tetrahydrofuran. The preferred solvent in this step is one or more solvent(s) selected from tetrahydrofuran, dimethylformamide, dimethylacetamide, N-methyl-2-pyrrolidone, dichloromethane, acetonitrile, ethyl acetate, and mixtures of these. Most preferably, the solvent is tetrahydrofuran.

The base, when used to perform the reaction of step (viii), as defined by Scheme 8, may be any suitable base that would be known to a person of skill in the art or can be determined for this type of chemical transformation. The base can be for example, sodium carbonate (Na$_2$CO$_3$), potassium carbonate (K$_2$CO$_3$), cesium carbonate (Cs$_2$CO$_3$), potassium phosphate tribasic (K$_3$PO$_4$), sodium phosphate tribasic (Na$_3$PO$_4$), N,N-diisopropylethylamine (DIPEA), triethylamine (Et$_3$N), sodium acetate (NaOAc), potassium acetate (KOAc), N-methylmorpholine (NMM) and 4-Dimethylaminopyridine (DMAP), or mixtures thereof. The preferred base in this process is one or more bases selected from K$_2$CO$_3$, Cs$_2$CO$_3$, K$_3$PO$_4$, DIPEA, NMM, DMAP, and Et$_3$N. Most preferably the reaction is performed in the presence of N-methylmorpholine (NMM).

The reaction of step (viii), as defined by Scheme 8, is performed in the presence of a coupling agent. The coupling agent should be known to a person of skill in the art or can be determined. E.g. the coupling agents may be one or more coupling agents selected from N,N'-carbonyldiimidazole (CDI), N-Ethyl-N-(3-dimethylaminopropyl)carbodiimide (EDC), N,N,N',N'-tetramethyl-O-(1H-benzotriazol-1-yl) uronium hexafluorophosphate (HBTU), 1-[Bis(dimethylamino)methylene]-1H-1,2,3-triazolo[4,5-b]pyridinium 3-oxid hexafluorophosphate (HATU), hydroxybenzotriazole (HOBt), Isobutyl carbonochloridate (IBCF), phosphoryl bromide (POBr$_3$), phosphoryl chloride (POCl$_3$), 2,4,6-Tripropyl-1,3,5,2,4,6-Trioxatriphosphorinane-2,4,6-Trioxide (T3P), 2-Chloro-4,6-dimethoxy-1,3,5-triazine (C DMT), benzotriazol-1-yl-oxytripyrrolidinophosphonium hexafluorophosphate (PyBOP), 4-(4,6-Dimethoxy-1,3,5-triazin-2-yl)-4-methylmorpholinium chloride (DMTMM) and N,N, N'—N'-Tetramethyl-O-(benzotriazol-12-yl)uronium tetrafluoroborate (TBTU), N,N'-Dicyclohexylcarbodiimide (DCC), Fluoro-N,N,N',N'-tetramethylformamidinium hexafluorophosphate (TFFH), Bis(Tetramethylene)Fluoroformamidinium hexafluorophosphate (BTFFH), 2-Bromo-1-ethyl-pyridinium tetrafluoroborate (BEP), Tri(dimethylamino)benzotriazol-1-yloxyphosphonium hexafluorophosphate (BOP), 7-Azabenzotriazol-1-yloxytris (dimethylamino)phosphonium hexafluorophosphate (AOP), and Ghosez's reagent (1-Chloro-N,N,2-trimethyl-1-propenylamine). Preferred coupling agent(s) in this reaction is one or more coupling agents selected from CDI, EDC, HBTU, HATU, HOBt, IBCF, POBr$_3$, POCl$_3$, T$_3$P, CDMT, PyBOP, DCC, TFFH, BTFFH, BEP, BOP, AOP, Ghosez's reagent and DMTMM. Most preferably the coupling agent is 2-chloro-4,6-dimethoxy-1,3,5-triazine (CDMT).

The reaction of step (viii), as defined by Scheme 8, is preferably performed, by reacting, in DMF, the compound of formula (3), N-methylmorpholine and 2-Chloro-4,6-dimethoxy-1,3,5-triazine at a temperature of about 0° C. The reaction mixture is stirred, preferably for 1 h or until the reaction is substantially complete, followed by addition of a compound of formula (IB). The reaction mixture is warmed to ambient temperature, preferably the reaction mixture is stirred at ambient temperature for 15-25 h, or until deemed complete.

The compound of formula (4), which results from the coupling of a compound of formula (IB) with a compound of formula (3) can be converted to Compound X. The conversion, i.e. deprotection, of the ester group $R^2$ in a compound of formula (4), to the carboxylic acid group in Compound X, can be performed under a condition selected from addition of acid, base, reduction in the presence of a catalyst and hydrogen, or an acid and hydrosilane. Depending on the $R^2$ group employed, the conversion of the ester group to the free acid (COOH) group, in Compound X, can be performed under conditions known to a person of skill in the art or can be determined. For example, conditions like those used for the deprotection of the ester group to form the carboxylic acid as described in PCT/US2015/022011, example 138. The $R^2$ group is selected from branched or linear $C_1$-$C_7$-alkyl, benzyl, $C_1$-$C_4$-alkoxy substituted benzyl, CH(aryl)$_2$. Preferably, $R_2$ is branched or linear $C_1$-$C_7$-alkyl, CH(aryl)$_2$. Preferably, $R^2$ is CH(aryl)$_2$, most preferably CH(C$_6$H$_5$)$_2$.

Preferably, the reaction is performed by addition of an acid, wherein the acid is selected from acetic acid, trifluoroacetic acid, bromoacetic acid, chloroacetic acid, formic acid, methanesulfonic acid, hydrochloric acid, and sulfuric acid. Preferably the acid is a carboxylic acid, more preferably trifluoroacetic acid and optionally, in the presence of a cation scavenger. Preferably, the acid is a carboxylic acid. The cation scavenger should be known to a person of skill in the art or can be determined. Scavengers commonly employed by those normally skilled in the art include, but are not limited to, anisole, cumene, 2,6-di-t-butyl phenol, resorcinol, p-t-butyl phenol, 4-(2-propyl)-phenol, phenol, thioanisole, m-cresol, p-cresol, dimethyl sulfide, 1,4-butanedithiol, 1,2-ethanedithiol, 2-mercaptoethanol, bis(hydroxymethyl)disulfide, D-penicillamine, cysteine, triethylsilane, and triisopropylsilane. Preferably, the cation scavenger is anisole.

The cation scavenger serves as a scavenger for the resultant alkyl carbocation that is formed in this deprotection step. The alkyl carbocation may readily react with the carboxylic acid, maintaining an equilibrium of the acid and ester, and may alkylate other nucleophiles, producing undesired byproducts and reducing the overall yield of Compound X. Presence of the acid scavenger reduces this effect.

Suitable solvents used for the reaction can be any polar aprotic solvent. For example, the solvent is one or more solvents selected from 2-methyltetrahydrofuran, tetrhydrofuran (THF), dichloromethane (DCM), chlorobenzene, and 1,2-dichloroethane. Preferably, the solvent is dichloromethane.

The reaction outlined in step (ix), as defined by Scheme 8, is preferably performed, by reacting in dichloromethane, at about 0 PC, a compound of formula (4) with trifluoroacetic acid and anisole. The reaction mixture is preferably allowed to warm to ambient temperature and stirred for 15-20 h, or until the reaction is deemed complete.

It is a further aspect of the present invention, to provide a compound of formula (3), synthesised as outlined in Scheme 9.

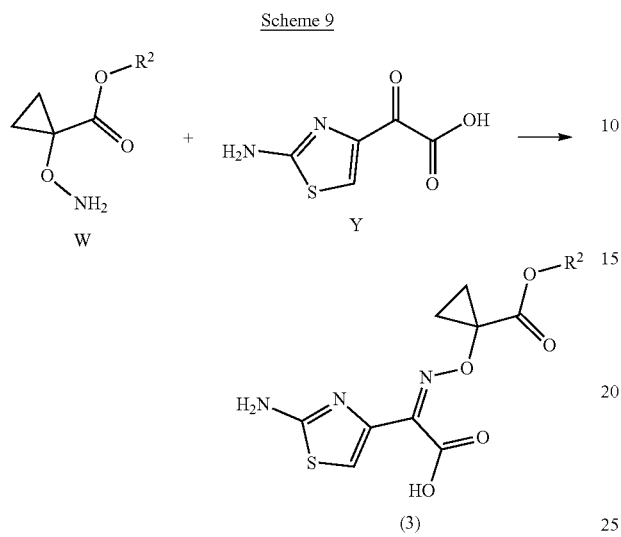

The compound of formula (W) can be prepared using a procedure analogous to that described in US 2011/0190254. The compound of formula (Y) is commercially available. In a preferred aspect, the compound of formula (3) is obtained by reacting compound Y and a compound of formula W, in a solvent, with a suitable base.

Patent application PCT/US2015/022011 describes an analogous transformation for the preparation of Compound X from a compound of formula (4), for example, on page 45 of the application as filed. Surprisingly, the current reaction conditions developed for the synthesis of Compound X from compounds of Formula (3) avoid the use of nitrogen protecting groups in steps (viii) and (ix) of scheme 8 and thus contributes to the overall improved efficiency of the process of the present invention.

Suitable solvents used for the reaction of Scheme 9 can be any polar solvent. For example, the solvent is one or more solvents selected from tetrahydrofuran (THF), dimethylformamide (DMF), dimethylacetamide (DMAc), N-methyl-2-pyrrolidone (NMP), N-butyl-2-pyrrolidone, dichloromethane (DCM), acetonitrile, ethanol, methanol, ethyl acetate, n-propanol, 2-propanol, n-butanol, 2-butanol, tert-butanol, and 2-methyl-tetrahydrofuran. The preferred solvent in this step is one or more solvent(s) selected from tetrahydrofuran, dimethylformamide, dimethylacetamide, N-methyl-2-pyrrolidone, dichloromethane, acetonitrile, ethyl acetate and ethanol. Most preferably, the solvent is dimethylacetamide.

The base used to perform the reaction of Scheme 9 may be any suitable base, such as a tertiary amine.

The tertiary amine is selected from optionally substituted trialkylamines or optionally substituted aromatic amines, or mixtures thereof. Suitable amines include, for example, triethylamine, tri-n-propylamine, tri-n-butylamine. N,N-diisopropylethylamine, N,N-dimethylcyclohexylamine, pyridines (including methyl substituted pyridine (2-, 3-, or 4-picoline, 2,6-lutidine)), pyrazines, pyrroles, purines, pyrimidines. Preferably, the base is triethylamine.

The reaction as outlined in Scheme 9, is preferably performed, by reacting in dimethylacetamide, a compound of formula (W), with compound Y in the presence of triethylamine. The reaction mixture is stirred at ambient temperature for 3-6 h, or until complete conversion of starting material is observed.

Preparation of Compound of Formula (VII)

It is a further aspect of the present invention to provide a compound of formula (VII), wherein R is branched or linear $C_1$-$C_7$ alkyl, benzyl, or $C_1$-$C_4$-alkoxy substituted benzyl, and X is selected from the group consisting of halide, carboxylate, and sulfonate, synthesised as outlined in Scheme 10.

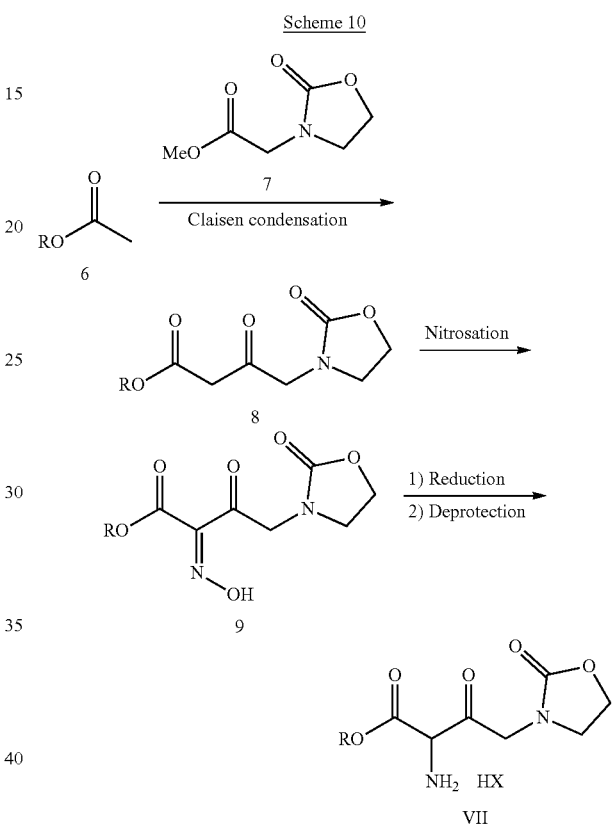

The β keto ester compound of formula (8) can be synthesized from a commercially available compound of formula (6) and the compound of formula (7). Depending on the R group employed, the skilled person would know how to synthesize the compound of formula (6), if not commercially available, using common general knowledge. The reaction takes place via a Claisen condensation (or cross condensation when R is not methyl) and is known to one skilled in the art. Claisen condensation reactions are commonly known as reactions that occur between two esters, or between one ester and another carbonyl compound, in the presence of a strong base, to produce an enolate from at least one ester, resulting in the production of a β-keto ester or a β-diketone.

The base used to perform the reaction may be any non-nucleophilic, preferably hindered base. Such bases include, for example, alkali metal amides, alkoxides, and hydrides. Preferably, the base is lithium bis(trimethylsilyl) amide.

The compound of formula (7) can be synthesised according to Fryer, et al., *J. Org. Chem.* 1991, 56, 3715-3719.

Next, the compound of formula (8) is converted to a compound of formula (9) by a nitrosation reaction. The manner in which the β-keto ester, i.e. the compound of formula (8), is nitrosated to the 3-keto-2-oximino ester compound of formula (9) can be carried out according to standard methods of organic chemistry known in the art. Such methods are described for e.g., in Blatt, Organic Syntheses, Collective Vol. 2, John Wiley & Sons, New York, pp. 204-208; Baumgarten, Organic Syntheses, Collective Vol. 5, John Wiley & Sons, New York, pp. 32-35 and 373-375; and Adkins, et al., *J. Am. Chem. Soc.* 1938, 60, 1328-1331.

The compound of formula (8) can be nitrosated, for example, with an alkyl nitrite such as isoamyl nitrite, or an aryl nitrite, such as phenyl nitrite; or, more preferably, in aqueous solution with nitrous acid or a salt thereof, in presence of an acid. Preferred nitrites are sodium nitrite, potassium nitrite, magnesium nitrite, particularly preferred is sodium nitrite. Preferred acids are hydrochloric acid, acetic acid or other carboxylic acids of formula R*—COOH where R* can be $C_1$-$C_6$ alkyl, H, or $C_1$-$C_6$ haloalkyl, sulfuric acid, and nitrosulfuric acid, or combinations of such acids; particularly preferred is acetic acid.

The nitrosation conditions that have been found to be particularly suitable are treatment of the β-keto ester compound of formula (8) with sodium nitrite and acetic acid.

The compound of formula (9) is converted to a compound of formula (VII) in a 2-step process, comprising the steps of, aa) reducing the compound of formula (9), followed by amine protection, to produce a compound of formula (9a),

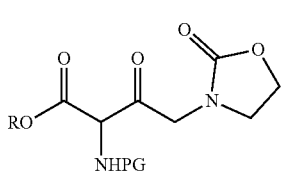

wherein R is branched or linear $C_1$-$C_7$ alkyl, benzyl, $C_1$-$C_4$-alkoxy substituted benzyl, and PG is selected from tert-butyloxycarbonyl (Boc), benzyloxycarbonyl (Cbz), fluorenylmethyloxycarbonyl (Fmoc), methyloxycarbonyl, ethyloxycarbonyl, allyloxycarbonyl, phenyloxycarbonyl, formyl, acetyl or benzyl, followed by, bb) deprotection of the compound of formula (9a) to produce a compound of formula (VII).

The hydroxyl imine (oxime) group in the compound of formula (9) can be reduced to the corresponding amine, and subsequently protected (acetylated) according to standard methods of organic chemistry known in the art. These include, for example, reduction in the presence of a catalyst and hydrogen, and reduction in the presence of a metal, for example, zinc. These methods are described, for example, in Gregory, et al., *J. Chem. Soc.* 1951, 2453-2456.

Preferably, the compound of formula (9) is reduced by zinc, in the presence of (Boc)$_2$O under acidic conditions, to provide the compound of formula (9a) wherein PG is —C(O)—O-tButyl. Preferably, the reaction mixture is heated. The compound of formula (9a) is subsequently reacted with an acid, preferably a hydrohalic acid, more preferably hydrochloric acid, to produce the compound of formula (VII).

Alternative Synthesis of Compound of Formula (VII)

The compound of formula (VII) can alternatively be synthesised according to Scheme 11.

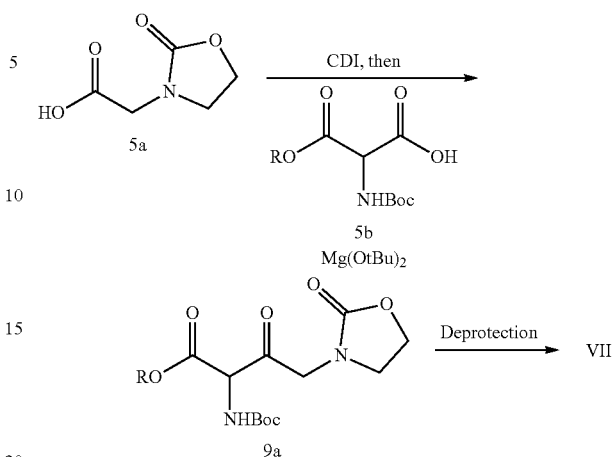

The compound of formula (VII) can be synthesised in shorter reaction times and in fewer reaction steps, as outlined in Scheme 11.

The compound of formula (9a) can be synthesised from commercially available compound 5a. Compound 5a is reacted with a coupling agent, such as CDI, resulting in an activated intermediate, which is then subsequently reacted with the compound of formula (5b) and Mg(OtBu)$_2$ to produce the compound of formula (9a), followed by deprotection of the compound of formula (9a), as set out in Scheme 11, to give the compound of formula (VII).

Thus, a further aspect of the present invention is the provision of a compound of formula (VII), wherein R is branched or linear $C_1$-$C_7$-alkyl, benzyl, or $C_1$-$C_4$-alkoxy substituted benzyl, and X is selected from the group consisting of halide, carboxylate, and sulfonate, which can be synthesised as outlined in Scheme 11.

The compound of formula 5b can be synthesised according to known literature procedures. These methods are described, for example, in Seebach, et al., *Helv. Chim. Acta* 1998, 81, 1845-1895.

The reaction is carried out by reacting, at ambient temperature, the compound of formula (5a) with a coupling agent, preferably CDI, and stirring until the reaction is substantially complete, or about 3 hours.

To the reaction mixture is added the compound of formula (5b) and a non-nucleophilic base such as potassium t-butoxide or Mg(OtBu)$_2$, and the mixture is subsequently stirred at ambient temperature for about 24 hours or until the reaction is substantially complete.

General Terms

The term "PG", refers to a nitrogen protecting group as defined herein.

The term "protecting group" or "nitrogen protecting group" refers to a moiety that may be present and should protect the functional groups concerned against unwanted secondary reactions, such as acylations, etherifications, esterifications, oxidations, solvolysis, and similar reactions. Suitable protecting groups and methods of introducing them, using them, and removing them are well known in the art. It is a characteristic of protecting groups that they lend themselves readily, i.e. without undesired secondary reactions, to removal, typically by solvolysis, reduction, photolysis or also by enzyme activity, for example under conditions analogous to physiological conditions, and that they are not present in the end-products. The specialist knows, or can easily establish, which protecting groups are suitable with the reactions mentioned hereinabove and hereinafter. Preferably, if two or more protecting groups are present in one intermediate mentioned herein, they are chosen so that, if one of the groups needs to be removed, this can be done selectively, e.g. using two or more different protecting groups that are cleavable under different conditions, e.g. one class by mild hydrolysis, the other by hydrolysis under harder conditions, one class by hydrolysis in the presence of an acid, the other by hydrolysis in the presence of a base, or one class by reductive cleavage (e.g. by catalytic hydrogenation), the other by hydrolysis, or the like.

Suitable nitrogen protecting groups are conventionally used in peptide chemistry and are described e.g. in the relevant chapters of standard reference works such as J. F. W. McOmie, "Protective Groups in Organic Chemistry", Plenum Press, London and New York 1973; T. W. Greene and P. G. M. Wuts, "Greene's Protective Groups in Organic Synthesis", Fourth Edition, Wiley, New York 2007; in "The Peptides"; Volume 3 (editors: E. Gross and J. Meienhofer), Academic Press, London and New York 1981, and in "*Methoden der organischen Chemie*" (Methods of Organic Chemistry), Houben Weyl, 4th edition, Volume 15/I, Georg Thieme Verlag, Stuttgart 1974.

Suitable nitrogen protecting groups generally comprise: $C_1$-$C_6$-alkyl, preferably $C_1$-$C_4$-alkyl, more preferably $C_1$-$C_2$-alkyl, (e.g. acetyl, allyl, teributyl) most preferably $C_1$-alkyl which is mono-, di- or tri-substituted by trialkylsilyl-$C_1$-$C_7$-alkoxy (eg. trimethylsilyethoxy), aryl, preferably phenyl, or an heterocyclic group (e.g., benzyl, cumyl, benzhydryl, pyrrolidinyl, trityl, pyrrolidinylmethyl, 1-methyl-1,1-dimethylbenzyl, (phenyl)methylbenzene) wherein the aryl ring or the heterocyclic group is unsubstituted or substituted by one or more, e.g. two or three, residues, e.g. selected from the group consisting of $C_1$-$C_7$-alkyl, hydroxy, $C_1$-$C_7$-alkoxy, $C_2$-$C_8$-alkanoyl-oxy, halogen, nitro, cyano, and $CF_3$; aryl-$C_1$-$C_2$-alkoxycarbonyl (preferably phenyl-$C_1$-$C_2$-alkoxycarbonyl (eg. benzyloxycarbonyl (Cbz), benzyloxymethyl (BOM), pivaloyloxymethyl (POM)); $C_1$-$C_{10}$-alkenyloxycarbonyl; $C_1$-$C_6$alkylcarbonyl (eg. acetyl or pivaloyl); $C_6$-$C_{10}$-arylcarbonyl; $C_1$-$C_6$-alkoxycarbonyl (eg. teributoxycarbonyl (Boc), methylcarbonyl, trichloroethoxycarbonyl (Troc), pivaloyl (Piv), allyloxycarbonyl); $C_6$-$C_{10}$-aryl$C_1$-$C_6$-alkoxycarbonyl (e.g. 9-fluorenylmethyloxycarbonyl (Fmoc)); allyl or cinnamyl; sulfonyl or sulfenyl; succinimidyl group, silyl groups (e.g. triarylsilyl, trialkylsilyl, triethylsilyl (TES), trimethylsilylethoxymethyl (SEM), trimethylsilyl (TMS), triisopropylsilyl or tert-butyldimethylsilyl). Preferred nitrogen protecting groups are disclosed herein, and include carbamates such as benzyloxycarbonyl (Cbz), fluorenylmethyloxycarbonyl (Fmoc), methyloxycarbonyl, ethyloxycarbonyl, allyloxycarbonyl and teributoxycarbonyl (Boc), as well as benzyl, methoxybenzyl, benzyloxymethyl (BOM), and pivaloyloxymethyl (POM).

Alkyl is defined as a radical or part of a radical is a straight or branched (one or, if desired and possible, more times) carbon chain, and is especially $C_1$-$C_7$-alkyl, preferably $C_1$-$C_4$-alkyl.

The term "$C_1$-$C_7$"—defines a moiety with up to and including maximally 7, especially up to and including maximally 4, carbon atoms, said moiety being branched (one or more times) or straight-chained and bound via a terminal or a non-terminal carbon. $C_1$-$C_7$-alkyl, for example, is n-pentyl, n-hexyl or n-heptyl, methyl, ethyl, n-propyl, isopropyl, n-butyl, isobutyl, sec-butyl, tert-butyl, in particular methyl, ethyl, n-propyl, isopropyl, n-butyl, isobutyl, sec-butyl, tert-butyl.

The term "alkoxy", defined as being a radical or part of a radical, refers to alkyl-O—, wherein the term alkyl is as defined herein, and includes, for example, $C_1$-$C_7$-alkoxy, for example, methoxy, ethoxy, n-propyloxy, isopropyloxy, n-butyloxy, isobutyloxy, sec-butyloxy, tert-butyloxy and also includes corresponding pentyloxy, hexyloxy and heptyloxy radicals. $C_1$-$C_4$ alkoxy is preferred.

Halide is preferably fluoride, chloride, bromide or iodide, most preferably, chloride, bromide or iodide.

Aryl being a radical or part of a radical is, for example $C_{6-10}$aryl, and is, preferably a mono- or polycyclic, especially monocyclic, bicyclic or tricyclic aryl moiety with 6 to 10 carbon atoms, preferably phenyl, and which can be unsubstituted or substituted, on the aromatic ring, by one or more substituents independently selected from for example, $C_1$-$C_4$-alkyl, $C_1$-$C_4$-alkoxy-$C_1$-$C_4$-alkyl or $C_1$-$C_4$-alkoxy.

The term $C_1$-$C_4$-alkoxy-$C_1$-$C_4$-alkyl refers to a radical of the formula —Rb—O—Ra where Ra is a $C_1$-$C_7$alkyl radical and Rb is a $C_1$-$C_7$ alkyl radical as defined above. The oxygen atom may be bonded to any carbon atom in either alkyl radical. Examples of $C_1$-$C_4$alkoxy-$C_1$-$C_4$-alkyl include, but are not limited to, methoxy-methyl, methoxy-ethyl, ethoxy-ethyl.

The term $C_1$-$C_4$-alkoxy substituted benzyl refers to a benzyl radical which is substituted on the aromatic ring, preferably at the 4-position, with a $C_1$-$C_4$-alkoxy group, as defined herein.

The term "amine" or "amino" should be understood as being broadly applied to both a molecule, or a moiety or functional group, as generally understood in the art, and may be primary, secondary, or tertiary. The term "amine" or "amino" includes compounds where a nitrogen atom is covalently bonded to at least one carbon, hydrogen or heteroatom. The terms include, for example, but are not limited to, "alkyl amino," "arylamino," "diarylamino," "alkylarylamino," "alkylaminoaryl," "arylaminoalkyl," "alkaminoalkyl," "amide," "amido," and "aminocarbonyl."

The term "alcohol solvent(s)" should be understood, as generally understood in the art, and may be primary, secondary, or tertiary. The term "alcohol solvent(s)" includes compounds that are branched or linear $C_1$-$C_4$ alcohols. The term includes, for example, but is not limited to, methanol, ethanol, n-propanol, 2-propanol, n-butanol, 2-butanol, tert-butanol.

The term aromatic hydrocarbon refers to a solvent, for example, $C_{6-10}$aryl, and is, preferably a mono- or polycyclic, especially monocyclic, bicyclic or tricyclic aryl moiety with 6 to 10 carbon atoms, and which can be unsubstituted or substituted, on the aromatic ring, by one or more substituents independently selected from, for example, $C_1$-$C_4$-alkyl. The term aromatic hydrocarbon includes, for example, but is not limited to, benzene, toluene, xylene, naphthalene, mesitylene.

The term organophosphorus reagent refers to an organic compound containing at least one phosphorus atom, such as phosphinic halides. For example, the term organophosphorus reagent includes, but is not limited to, diphenylphosphinic chloride, dialkylphosphinic chloride, wherein alkyl is as defined herein. Preferably, the organophosphorus reagent is diphenylphosphinic chloride.

The term hydrosilane refers to an organic compound containing at least one Si—H bond. For example, the term hydrosilane includes $R_3SiH$, $R_2SiH_2$, $RSiH_3$. Each R group can be idependently selected from alkyl or aryl, as defined herein. For example, the hydrosilane can be $Ph_2(CH_3)SiH$, $Et_3SiH$, or $Ph_2SiH_2$.

The term "chiral" refers to molecules which have the property of non-superimposability on their mirror image partner.

The compounds of the present invention can possess one or more asymmetric centers. The preferred absolute configurations are as indicated herein specifically.

In the formulae of the present application the term " ⁄ " on a $C$-$sp^3$ indicates the absolute stereochemistry, either (R) or (S).

In the formulae of the present application the term " ⁄⁄ " on a $C$-$sp^3$ indicates the absolute stereochemistry, either (R) or (S).

For the purposes of the present invention, the term "enantiomerically enriched" means that one enantiomer is present in greater quantity than its optical antipode (opposite enantiomer) in a sample, wherein the predominant enantiomer is present in a range of >50% and ≤100%. The ee (enantiomeric excess) value is calculated as: ([Enantiomer1]−[Enantiomer2])/([Enantiomer1]+[Enantiomer2])=ee value. For example, the compound of formula (VIIc) has an ee value of greater than 99.5%.

The term "diastereomerically enriched" or "diastereomeric purity" or "diastereomeric excess" is the proportion of one diastereomer in a mixture with its other diastereomers in a range, wherein, in an enriched preparation, one diastereomer is in the range of >50% and 100%. For example, the compound of formula (VIIc) has a diastereomeric excess of VIIIc:VIId of 97.6%.

Unless otherwise indicated the names of molecules and groups are intended to include all possible diastereomers, the two enantiomers of any diastereomer also being included.

The term stereoisomer means one of the absolute configurations of a single organic molecule having at least one asymmetric carbon. Included within the definition of a stereoisomer are enantiomers and diasteromers.

The term "ligand" means any compound, achiral or chiral, that can form a complex with a transition metal. Preferably, the ligand is a chiral ligand and can be, for example, BINAP, CHIRAPHOS, SYNPHOS, BnDPAE, TsDPEN, $C_6F_5SO_2DPEN$, $CF_3SO_2DPEN$, N-trifluoromethanesulfonyl-1,2-cyclohexanediamine. The skilled person will readily understand what stereochemical configuration of the chiral ligand is needed, depending on the desired stereochemical confirguration of the resulting product.

The term "catalyst" as used herein refers to a chemical agent that enhances the rate of a chemical reaction by lowering the activation energy for the chemical reaction. The catalyst can be a heterogeneous catalyst or a homogenous catalyst.

The term "heterogeneous catalyst" refers to a catalyst that does not dissolve in a reaction medium and is often supported on a carrier, typically although not necessarily a substrate comprised of an inorganic material, for example, a porous material such as carbon, silicon and/or aluminum oxide.

The term "homogeneous catalyst" refers to a catalyst that is soluble in a reaction medium.

The term "hydrogenation" is used to describe a chemical reaction which refers to the action of reducing another compound in the presence of hydrogen. The source of hydrogen can be selected from gaseous hydrogen ($H_2$), hydrogen donors (transfer hydrogenation, e.g. formic acid or salts thereof), hydride reagent ($BH_3$, $B_2H_6$, $NaBH_4$) or the like.

The term "room temperature" or "ambient temperature" as used herein, unless specified otherwise, means a temperature from 15 to 30° C., such as from 20 to 30° C., particularly such as from 20 to 25° C.

'Salt' or 'salts', as used herein refers to the salts of any of the intermediates mentioned herein, where salts are not excluded for chemical reasons the skilled person will readily understand. They can be formed where salt forming groups, such as basic or acidic groups, are present that can exist in dissociated form at least partially, e.g. in a pH range from 4 to 10 in aqueous solutions, or can be isolated especially in solid, especially crystalline, form.

Such salts are formed, for example, as acid addition salts, preferably with organic or inorganic acids, from compounds or any of the intermediates mentioned herein with a basic nitrogen atom (e.g. imino or amino), especially the pharmaceutically acceptable salts. Suitable inorganic acids are, for example, halogen acids, such as hydrochloric acid, sulfuric acid, or phosphoric acid. Suitable organic acids are, for example, carboxylic, phosphonic, sulfonic or sulfamic acids, for example acetic acid, propionic acid, lactic acid, fumaric acid, succinic acid, citric acid, amino acids such as glutamic acid or aspartic acid, maleic acid, hydroxymaleic acid, methylmaleic acid, benzoic acid, methane- or ethane-sulfonic acid, ethane-1,2-disulfonic acid, benzenesulfonic acid, 2-naphthalenesulfonic acid, 1,5-naphthalenedisulfonic acid, N-cyclohexylsulfamic acid, N-methyl-, N-ethyl- or N-propyl-sulfamic acid, or other organic protonic acids, such as ascorbic acid.

Salts of compounds of the present invention having acid groups may be formed, for example, by treating the compounds with basic compounds, such as alkali metal salts of suitable organic carboxylic acids, e.g. the sodium salt of 2-ethylhexanoic acid, with inorganic alkali metal or alkaline earth metal compounds, such as the corresponding hydroxides, carbonates or hydrogen carbonates, such as sodium or potassium hydroxide, carbonate or hydrogen carbonate, with corresponding calcium compounds or with ammonia or a suitable organic amine, including primary, secondary and tertiary amines; stoichiometric amounts or only a small excess of the salt-forming agent is preferably used. Acid addition salts of compounds of the present invention are obtained in customary manner, e.g. by treating the compounds with an acid or a suitable anion exchange reagent. When a basic group and an acid group are present in the same molecule, any of the intermediates mentioned herein may also form internal salt. Internal salts of compounds of the present invention containing acid and basic salt-forming groups, e.g. a free carboxy group and a free amino group, may be formed, e.g. by the neutralisation of salts, such as acid addition salts, to the isoelectric point, e.g. with weak bases, or by treatment with ion exchangers.

The compound of formula 2A may exist as a zwitterion. For example, the compound of formula 2A may show a protonated amino group and deprotonated carboxy group.

In view of the close relationship between the compounds and intermediates in free form and in the form of their salts, including those salts that can be used as intermediates, for example in the purification or identification of the compounds or salts thereof, any reference to "compounds", "starting materials" and "intermediates" hereinbefore and hereinafter is to be understood as referring also to one or more salts thereof or a mixture of a corresponding free compound, intermediate or starting material and one or more salts thereof, each of which is intended to include also any solvate or salt of any one or more of these, as appropriate and expedient and if not explicitly mentioned otherwise. Different crystal forms may be obtainable and then are also included.

The term Compound X, if not defined specifically, is to be understood both as the free acid and as a salt, especially a pharmaceutically acceptable salt, or solvate including hydrate thereof. Compound X, or a pharmaceutically acceptable salt, or solvate including hydrate thereof, can, e.g., be prepared in a manner known per se, for example as described in PCT/CN2016/099482, in particular, the arginine salt, sodium salt and hydrated solid forms of Compound X.

The term solvate refers to a molecular complex of a compound of the present invention (including pharmaceutically acceptable salts thereof) with one or more solvent molecules. Such solvent molecules are those commonly used in the pharmaceutical art, which are known to be innocuous to the recipient, e.g. water, ethanol, and the like. The term hydrate refers to the complex where the solvent molecule is water.

As used in this specification and the appended claims, the singular forms "a", "an", and "the" include plural referents unless the context clearly indicates otherwise.

Similarly, "comprise", "comprises", "comprising", "include", "includes" and "including" are interchangeable and not intended to be limiting.

Abbreviations
δ chemical shift
$^{13}$C-NMR carbon nuclear magnetic resonance
$^{1}$H-NMR proton nuclear magnetic resonance
Ac acetyl
AcOH acetic acid
aq aqueous
BPR back pressure regulator
BINAP (1,1'-binaphthalene-2,2'-diyl)bis(diphenylphosphine)
BnDPAE 2-(benzylamino)-1,2-diphenylethanol
Boc tert-butyloxycarbonyl
(Boc)$_2$O di-tert-butyl dicarbonate
br broad
br d broad doublet
br dd broad doublet of doublets
br m broad multiplet
br s broad singlet
Bu butyl
Bu$_4$NHSO$_4$ tetrabutylammonium hydrogensulfate
C$_6$F$_5$SO$_2$DPEN N-(2-amino-1,2-diphenylethyl)-2,3,4,5,6-pentafluorobenzenesulfonamide
Cbz-Cl benzyl chloroformate
CF$_3$SO$_2$DPEN N-(2-amino-1,2-diphenylethyl)-1,1,1-trifluoromethanesulfonamide
CHIRAPHOS bis(diphenylphosphino)butane
ClSO$_3$H chlorosulfonic acid
CoCl$_2$ cobalt(II) chloride
Cs$_2$CO$_3$ cesium carbonate
d deuterated (e.g. CHLOROFORM-d)
d doublet
de diastereomeric excess
DMAc dimethylacetamide
DME dimethoxyethane
DMF dimethylformamide
DMSO dimethylsulfoxide
DMSO-d$_6$ deuterated dimethylsulfoxide
EA ethyl acetate
ee enantiomeric excess
Eq./Equiv. equivalent
Et ethyl
Et$_3$N or NEt$_3$ triethylamine
EtOH ethanol
Fmoc 9-fluorenylmethyloxycarbonyl
g gram(s)
h hour(s)
H hydrogen atom/proton
H$_2$ hydrogen
H$_2$O water
HCl hydrochloric acid
HF hydrogen fluroide
HPLC high performance liquid chromatography
Hz hertz
IPA isopropyl alcohol (propan-2-ol)
IPAC isopropyl acetate
IPC in process control
[Ir(cod)(PCy$_3$)(Py)]$^+$ (1,5-cyclooctadiene)(pyridine)(tricyclohexylphosphine)-iridium(I)
J coupling constant
K kelvin
kg kilogram(s)
K$_2$CO$_3$ potassium carbonate
KHCO$_3$ potassium hydrogen carbonate/potassium bicarbonate
L litre(s)
LCMS liquid chromatography-mass spectrometry
LiHMDS lithium bis(trimethylsilyl)amide
m multiplet
M molarity/molar
Me methyl
mg milligram(s)
Mg(OtBu)$_2$ magnesium di-tert-butoxide
MgSO$_4$ magnesium sulfate
MHz megahertz
min minute(s)
ml milliliter
mmol millimole
mol mole(s)
mol % mole percent
Mpa megapascal
Ms mesyl (SO$_2$CH$_3$)
MsCl methanesulfonyl chloride
MTBE or TBME methyl tertbutylether
N$_2$ nitrogen
NaCl sodium chloride
NaHCO$_3$ sodium hydrogencarbonate/sodium bocarbonate
NaHMDS sodium bis(trimethylsilyl)amide
NaNO$_2$ sodium nitrite
Na$_2$SO$_4$ sodium sulfate
NBu$_4$$^+$ tetrabutylammonium
NH$_3$ ammonia
NH$_4$Cl ammonium chloride
NiCl$_2$ nickel(II) chloride
Ni(OAc)$_2$ nickel(II) acetate
NMP N-methyl-2-pyrrolidone
NMR nuclear magnetic resonance spectroscopy
Pd$_2$dba$_3$ tris(dibenzylideneacetone)dipalladium(0)
Pd/Al$_2$O$_3$ palladium on aluminum oxide
Pd/C palladium on carbon
Pd/CaCO$_3$ palladium on calcium carbonate
Pd(OAc)$_2$ palladium acetate
Pd(OH)$_2$ palladium hydroxide
PFA polytetrafluoroethylene
Ph phenyl
phos phosphine
ppm parts per million Pt/C platinium on carbon
Q-NMR quantitative
quin quintet
r/min revolutions per minute
RhCl(PPh$_3$)$_3$ chloridotris(triphenylphosphane)rhodium(I)
Rh/C rhodium on carbon
[Rh(cod)(PPh$_3$)$_2$]$^+$ bis(triphenylphosphine)(1,5-cyclooctadiene)rhodium(I)
s singlet
sept. septuplet
SYN PHOS [(5,6),(5',6')-bis(ethylenedioxy)biphenyl-2,2'-diyl]bis(diphenylphosphine)
sxt sextet
t triplet
1° C. temperature in celsius
TiCl$_3$ titanium(III) chloride
TFA trifluoroacetic acid
TLC thin-layer chromatography
TsDPEN N-tosyl-1,2-diphenylethylenediamine
tBu tertbutyl
THF tetrahydrofuran
w/w by weight
wt % percentage by weight
ZrCl$_4$ zirconium(IV) chloride General Experimental Details
Synthesis Generally, compounds according to the present disclosure can be synthesized by the routes described in the Schemes 1-11 as shown herein.

The skilled person will appreciate that the general synthetic routes detailed in the application show common reactions to transform the starting materials as required. When specific reactions are not provided the skilled person will know that such reactions are well known to those skilled in the art and appropriate conditions considered to be within the skilled person's common general knowledge. The starting materials are either commercially available compounds or are known compounds and can be prepared from procedures described in the organic chemistry art.

General Conditions

NMR spectra were run on Bruker AVANCE 400 MHz spectrometers using ICON-NMR, under TopSpin program control. Spectra were measured at 298K, unless indicated otherwise, and were referenced relative to the solvent resonance or tetramethylsilane resonance.

Instrumentation
HPLC Methods:
Column: Agilent Poroshell 3.0*75 mm, 2.7 um
Column temperature: 40° C.
Mobile phase: A 0.1% H$_3$PO$_4$ in water, Mobile phase B acetonitrile
Flow rate: 0.7 mL/min
Gradient: 10% acetonitrile to 90% acetonitrile in 11 min, hold 5 min, 90% acetonitrile to 10% acetonitrile in 0.1 min, hold 3 min
Detector: UV 210 nm
Chiral HPLC Methods:
Column: CHIRALCEL OZ-H 0.46 cm I.D.×15 cm L
Temperature: 35° C.
Mobile phase: Hexane/EtOH=85/15 (v/v)
Flow rate: 1.0 ml/min
Detector: Wave length UV 214 nm

EXAMPLES

The Following examples are merely illustrative of the present disclosure and they should not be considered as limiting the scope of the disclosure in any way, as these examples and other equivalents thereof will become apparent to those skilled in the art in the light of the present disclosure, and the accompanying claims.

Synthesis of Compound 8 (R=benzyl)

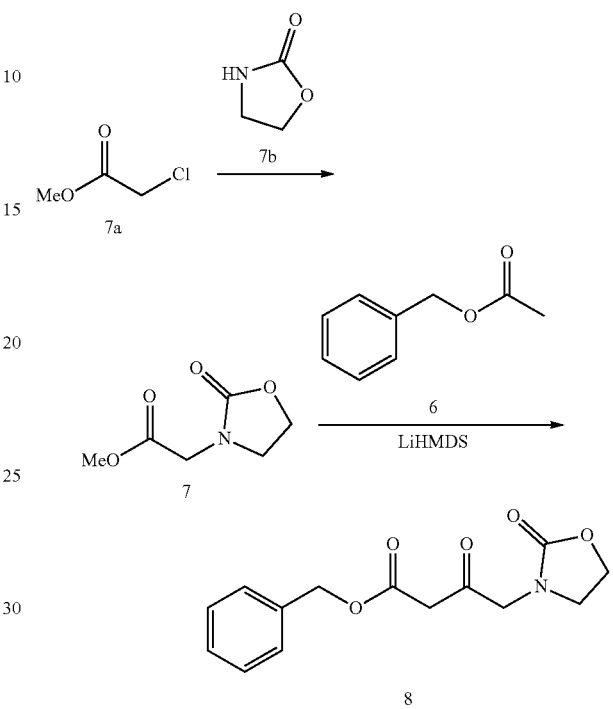

1.50 kg oxazolidin-2-one (7b) was charged into the reactor. 7.50 kg THF was charged and the stirring started. The mixture was cooled to 10-20° C. 2.18 kg potassium tert-butoxide was charged into 12.00 kg THF and stirred to dissolve.

The potassium tert-butoxide solution was added dropwise into the reactor while maintaining the temperature at 10-20° C. The reaction was stirred for 1-2 hrs at 10-20° C. after the addition. The solution of 2.36 kg methyl-2-chloroacetate (7a) in 3.00 kg of THF was added to the reactor while maintaining the temperature at 10-20° C. The reaction mixture was stirred for 16~18 h at 20~25° C. The IPC (in process control) showed completion of the reaction. The mixture was centrifuged and the wet cake was washed with 7.50 kg THF. The filtrate was concentrated and the crude 7 was provided as reddish brown liquid, which was used for the next step without further purification, $^1$H NMR (400 MHz, CHLOROFORM-d) δ ppm 3.65-3.71 (m, 2H) 3.74 (s, 3H) 4.02 (s, 2H) 4.34-4.45 (m, 2H).

The dried reactor was exchanged with N$_2$ three times. 3.71 kg LiHMDS solution in THF/Hep (1 M) and 1.30 kg THF were charged under nitrogen protection. The stirring was started and the solution was cooled to −70-60° C. The solution of 0.71 kg benzyl acetate (6) in 5.20 kg THF was added dropwisely at −70~−60° C., and the resulted mixture was stirred for ~1.5 h after the addition. The solution of 0.65 kg 7 in 3.90 kg THF was added dropwise while maintaining the temperature at −70~−60° C., then stirred for 30~40 minutes. The reaction mixture was warmed to 20~25° C. and stirring was continued for 0.5~1.0 h. IPC showed 6 was less than 1.0% (Otherwise, continue the reaction till IPC passes). The reaction mixture was poured into 13.65 kg aqueous citric acid below 10° C. The mixture was stirred for 15~20 minutes after the addition. Phases were separated and the organic layer was collected. The aqueous layer was extracted with EA (6.50 kg*2). The organic layer was combined, washed by 6.50 kg 28% NaCl solution and dried with 0.65 kg anhydrous MgSO$_4$. The mixture was filtered and the wet cake was washed with 1.30 kg EA. The filtrate was concentrated under vacuum to provide crude 8. The crude 8 was stirred in 2.60 kg MTBE at 20~25° C. for 1-1.5 h. The mixture was cooled to 0~10° C. and stirred for 1.5~2.0 h and filtered. The filter cake was washed with 0.65 kg pre-cooled MTBE and dried under vacuum (≤−0.096 Mpa) at 20~25° C. for 12-16 hrs till a constant weight to give 513 g of 8 as a white solid, Yield: 45%, HPLC purity 96.4%, $^1$H NMR (400 MHz, CHLOROFORM-d) δ ppm 3.48-3.55 (m, 1H) 3.56-3.63 (m, 2H) 3.66-3.74 (m, 1H) 4.17-4.26 (m, 2H) 4.31-4.44 (m, 2H) 5.12-5.24 (m, 2H) 7.30-7.44 (m, 5H).

Synthesis of Compound 9 (R=benzyl)

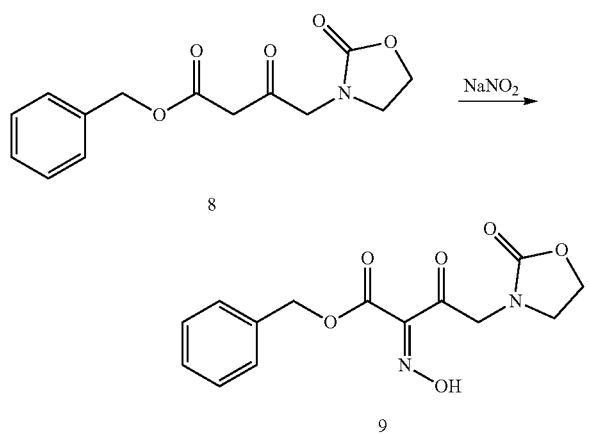

The dried reactor was charged with 3.75 kg HOAc and 1.50 kg 8. The stirring was started and the reaction mixture was cooled to 0-5° C. 3.53 kg aqueous NaNO$_2$ was added dropwise at 0-10° C., and the reaction mixture was stirred for 15~30 minutes after the addition. IPC showed 8 was less than 0.2%. The reaction mixture was treated with 7.50 kg EA and 7.50 kg water. Phases were separated and the organic layer was collected. The aqueous layer was extracted with EA (7.50 kg*2). The organic layers were combined, washed with 7.50 kg 28% NaCl solution, and concentrated under vacuum to provide crude 9. The crude 9 was slurried with 5.25 kg water at 10~20° C. for 3-4 hrs, and filtered. The wet cake was washed with 1.50 kg water. The solid was dried under vacuum (−0.096 Mpa) at 45~50° C. for 5-6 h till a constant weight to give 1.44 Kg of 9, yield: 86.9%, HPLC purity 92.9%, $^1$H NMR (400 MHz, CHLOROFORM-d) δ ppm 3.60-3.76 (m, 2H) 4.44 (t, J=8.07 Hz, 2H) 4.60 (s, 2H) 5.25-5.41 (m, 2H) 7.30-7.43 (m, 5H) 11.62 (br s, 1H).

Synthesis of Compound 9a (R=benzyl)

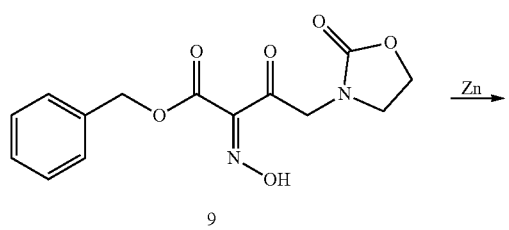

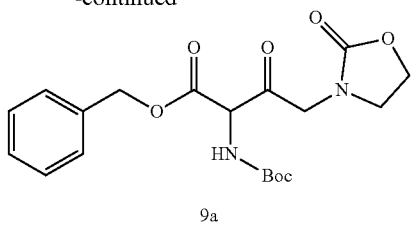

The dried reactor was charged with 0.58 kg Zn, 4.72 kg (Boc)$_2$O, 6.00 kg water, 1.20 kg NH$_4$Cl and 6.00 kg THF. The reaction mixture was stirred and heated to 50~55° C. The solution of 0.60 kg 9 in 4.20 kg THF was added dropwisely while maintaining the temperature at 50~55° C. The reaction mixture was stirred for 0.5~1.0 hrs after the addition. IPC showed 9 was less than 0.1%. The reaction mixture was treated with 1.50 kg ethyl acetate and stirred for 15~20 minutes. Phase was separated and the water layer was extracted by 1.50 kg ethyl acetate. The organic layers were combined, washed with 6.00 kg 28% NaCl solution and concentrated under vacuum to provide crude 9a. The crude 9a was stirred with 3.60 kg*2 n-heptane to remove excess (Boc)$_2$O. The residue was purified by silica gel chromatography column eluted with ethyl acetate:Heptane=1:1 to provide crude 9a solution. The solution was concentrated under reduced pressure to obtain crude 9a. The crude 9a was slurried with 1.80 kg MTBE for 2.0~3.0 hrs, filtered, and the wet cake was washed with MTBE. The solid was dried under vacuum (≤−0.096 Mpa) at 50~55° C. for 16~18 h till a constant weight to give 392 g of 9a as a white solid, Yield: 51%, HPLC purity 98.1%, $^1$H NMR (400 MHz, DMSO-d$_6$) δ ppm 1.17-1.57 (m, 9H) 3.39-3.61 (m, 2H) 4.20-4.45 (m, 3H) 5.10-5.32 (m, 3H) 5.75 (s, 1H) 7.38 (br s, 5H) 7.75-7.99 (m, 1H).

Synthesis of Compound (VII) (R=benzyl, X=Cl)

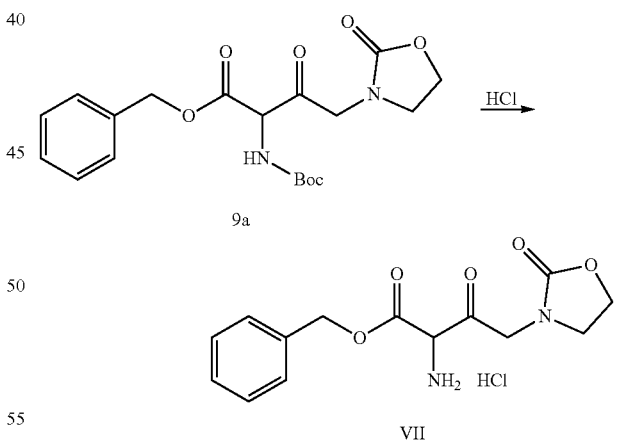

The dried reactor was charged with 13.0 kg HCl in IPA and the stirring was started. 1.33 kg 9a was charged in portions at 20~25° C. The mixture was stirred at 20~25° C. for 3~4 h. IPC showed 9a was less than 0.1%. The reaction solution was concentrated under vacuum 40~45° C. The residue was treated with 21.58 kg MTBE at 20~25° C. for 3~4 h. The mixture was filtered and the wet cake was washed with 2.60 kg MTBE. The solid was dried under vacuum (≤−0.096 Mpa) at 45~50° C. for 5~6 h till a constant weight to give 1.045 Kg of compound VII (R=benzyl, X=Cl) as a yellow solid, Yield: 93.7%, HPLC purity 99.2%, $^1$H NMR (400 MHz, DMSO-d$_6$) δ ppm 3.16-3.74 (m, 3H) 4.10-4.35 (m, 4H) 5.09-5.39 (m, 2H) 7.27-7.60 (m, 5H) 8.72 (br s, 2H).

Synthesis of Compound (VIII) (R=benzyl)

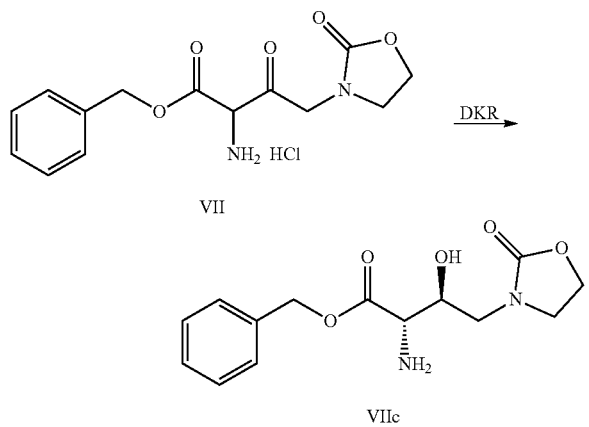

To an autoclave (3 L) were added VII (R=benzyl, X=Cl) (100 g, 304.2 mmol, 1.0 equiv.), DCM (2650 g, 26.5 equiv., w/w) and (S-BINAP)RuCl$_2$ (2.4 g, 3.04 mmol, 0.01 equiv.), successively. Air in the autoclave was replaced with N$_2$ 5 times. N$_2$ in the autoclave was was replaced with H$_2$ 5 times. The solution was stirred with 250~260 r/min and H$_2$ (2.1±0.1 MPa) at 40±5° C. for 24 h. The reaction mixture was filtered, and the filter cake was washed with DCM (400 g, 4.0 equiv., w/w). The filter cake was slurried with IPA (785 g, 7.85 equiv., w/w) and H$_2$O (40 g, 0.4 equiv., w/w) overnight (18~20 h). The mixture was filtered. The filter cake was washed with IPA (200 g, 2.0 equiv., w/w) and dried at 45±5° C. overnight (18~20 h). VIIc (R=benzyl) was obtained as off-white solid, 80.4 g, 79.9% yield, 95.5% purity, 97.6% de, >99.5% ee. $^1$H NMR (400 MHz, DMSO-d$_6$) δ ppm 3.34-3.38 (m, 2H) 3.50-3.52 (m, 1H) 3.60-3.62 (m, 1H) 4.18-4.24 (m, 4H) 5.23 (s, 2H) 6.16 (s, 1H) 7.32 (m, 5H) 8.74 (s, 1H).

Alternative Synthesis of Compound 9a (R=benzyl)

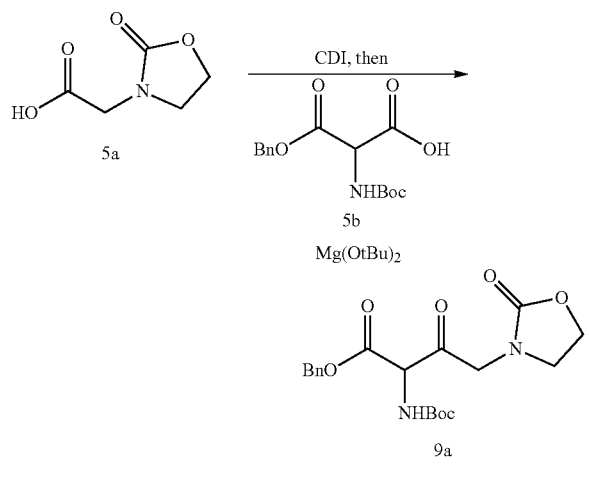

To a flask was added 5a (1.88 g, 12.93 mmol), THF (40 mL), and CDI (2.20 g, 13.58 mmol) at 25° C. The mixture was stirred for 3 h. To the reaction mixture was added 5b (2.00 g, 6.47 mmol), and Mg(OtBu)$_2$ (2.21 g, 12.93 mmol). The reaction mixture was stirred at 25° C. for 24 h. The reaction mixture was concentrated under vacuum to remove most of the THF solvent. To the concentrated solution was added MTBE (40 mL), followed by addition of an aqueous solution of HCl (1M, 60 mL) to adjust to pH=2~3. Two phases were separated, and the water phase was extracted with MTBE (20 mL). The combined organic phase was washed with aqueous NaHCO$_3$ (5%, 50 mL) and brine (20%, 40 mL). The organic phase was concentrated to a weight of ~19 g, and a lot of white solid was obtained in the concentration process. The suspension was cooled to 0° C., and filtered. The filter cake was washed with cold MTBE (5 mL) and dried under vacuum to obtain product 9a (1.6 g, 63% yield).

Synthesis of Compound (VIIe) (R=benzyl, PG=Cbz)

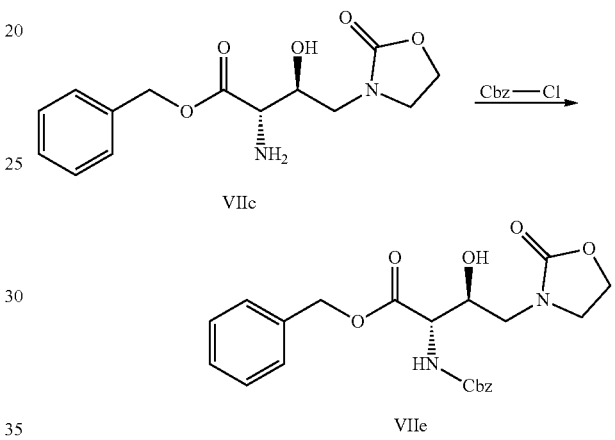

To a flask (5 L) were added VIIc (R=benzyl) (140 g, 423.2 mmol, 1.0 equiv.), H$_2$O (1273 g, 9.09 equiv., w/w) and toluene (2206 g, 15.76 equiv., w/w). The solution was stirred and cooled to 0~5° C. with ice bath. Then NaHCO$_3$ (78.4 g, 933 mmol, 2.22 equiv.) was added and CbzCl (89.6 g, 527 mmol, 1.24 equiv.) was dropped into the stirring solution, respectively. The solution was stirred at 30±5° C. overnight (18~20 h). Heptane (3612 g, 25.8 equiv., w/w) was added dropwise to the stirring solution over 1 h at 20~30° C. The mixture was filtered. The filter cake was washed with heptane (280 g, 2.00 equiv., w/w) and MTBE (377 g, 2.69 equiv., w/w), respectively. The filter cake was dried at 45±5° C. overnight (18~20 h). VIIe (R=benzyl, PG=Cbz) was obtained as an off-white solid, 169.4 g, 93% yield, 96.7% purity, 98% de, >99.5% ee, $^1$H NMR (400 MHz, DMSO-d$_6$) δ ppm 3.23-3.24 (m, 1H) 3.30 (m, 1H) 3.51-3.55 (m, 2H) 3.99 (s, 1H) 4.17-4.21 (m, 3H) 5.02-5.03 (m, 2H) 5.12 (s, 2H) 5.46-5.48 (d, 1H) 7.33-7.36 (m, 10H) 7.75-7.73 (d, 1H).

Synthesis of Compound (IV) (PG=Cbz)

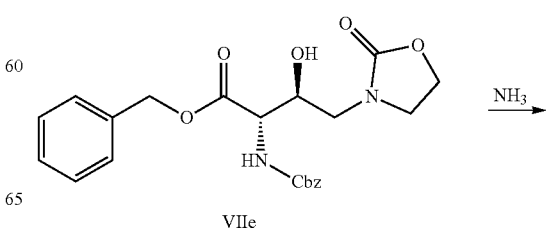

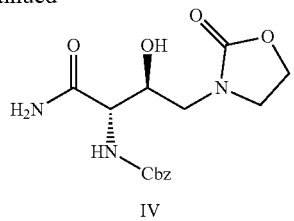

IV

VIIe (R=benzyl) (220 g, 513.5 mmol, 1.0 equiv.) was dissolved in THF (1464 g, 6.65 equiv., w/w). The solution was filtered. The filter cake was washed with THF (488 g, 2.22 equiv., w/w). The filtrate (VIIe) was collected. To an autoclave (3 L) were added the filtrate (VIIe). The reactor was cooled down to −75~−65° C. with dry-ice/EtOH bath, and bubbled with $NH_3$ for not less than 4 h. Then the solution was stirred at 25±5° C. with $NH_3$ (0.5~0.6 MPa) for 24 h. The autoclave was deflated to release $NH_3$. The reaction solution was concentrated with a rotary evaporator to remove THF until the residue was around 440 g. The residue was slurried with EA (2200 g, 10 equiv., w/w) at 70±2° C., then cooled to 25±5° C. and stirred for 16~18 h. The mixture was filtered. The filter cake was washed with EA (440 g). The filter cake was slurried with EA (1320 g, 6.00 equiv. w/w), and the temperature was raised to 70±2° C., then cooled to 25±5° C. and stirred for 16~20 h. The mixture was filtered. The filter cake was washed with EA, and dried at 50±5° C. overnight (18~20 h). IV (PG=Cbz) was obtained as off-white solid, 141 g, 81.5% yield, 99.1% purity, >99.5% assay, $^1$H NMR (400 MHz, DMSO-$d_6$) δ ppm 3.12-3.23 (m, 2H) 3.31 (br s, 1H) 3.56 (t, J=8.01 Hz, 2H) 3.88 (quin, J=6.02 Hz, 1H) 3.93-4.03 (m, 1H) 4.20 (t, J=8.01 Hz, 2H) 5.02 (s, 2H) 5.27 (d, J=5.87 Hz, 1H) 7.12 (s, 1H) 7.22-7.45 (m, 5H).

Synthesis of Compound (III) (PG=Cbz, LG=$SO_2CH_3$)

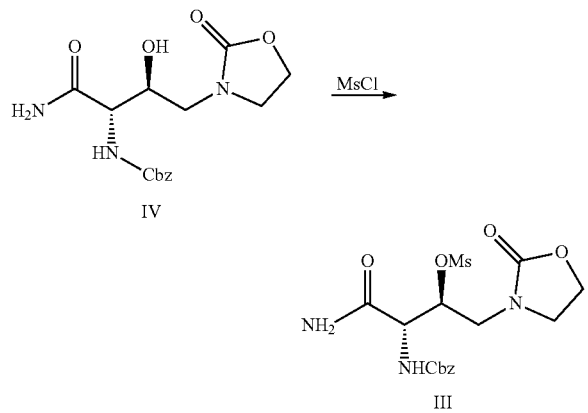

III

To a flask was added IV (PG=Cbz) (14.00 g, 41.50 mmol, 1.00 equiv), and dry 1,2-dimethoxyethane (300 mL) under $N_2$. The mixture was stirred at −5° C.~0° C. for 1 h to obtain a good suspension. MsCl (7.89 g, 68.89 mmol, 5.33 mL, 1.66 eq) in 1,2-dimethoxyethane (20.00 mL) was added dropwise during 30 min, and $Et_3N$ (12.60 g, 124.50 mmol, 17.26 mL, 3.00 eq) in 1,2-dimethoxyethane (20.00 mL) was added dropwise during 30 min side to side. The reaction mixture was stirred for additional 5 min at −5° C.~0° C., and was quenched with water (6 mL). The reaction mixture was concentrated to remove DME. The solid was slurried in water (250 mL) and MTBE (125 mL) for 1 h. The solid was collected by filtration, and then slurried in water (250 mL) for 1 hr. The solid was collected by filtration, and washed with water (25 mL) to give white solid. The solid was slurried in EA (150 mL) and dried in vacuum at 60° C. for 24 h to give III (PG=Cbz, LG=$SO_2CH_3$) (15.00 g, 36.11 mmol, 87.01% yield), $^1$H NMR (400 MHz, DMSO-$d_6$) δ ppm 3.17 (s, 3H) 3.26 (br d, J=15.04 Hz, 1H) 3.47-3.57 (m, 1H) 3.64 (br d, J=6.36 Hz, 2H) 4.22 (br dd, J=17.79, 8.50 Hz, 2H) 4.50 (br s, 1H) 4.95-5.17 (m, 3H) 7.21-7.56 (m, 5H) 7.43 (s, 1H) 7.63-7.89 (m, 2H).

Synthesis of Compound II (PG=Cbz, LG=$SO_2CH_3$, $M^+$=$NBu_4^+$)

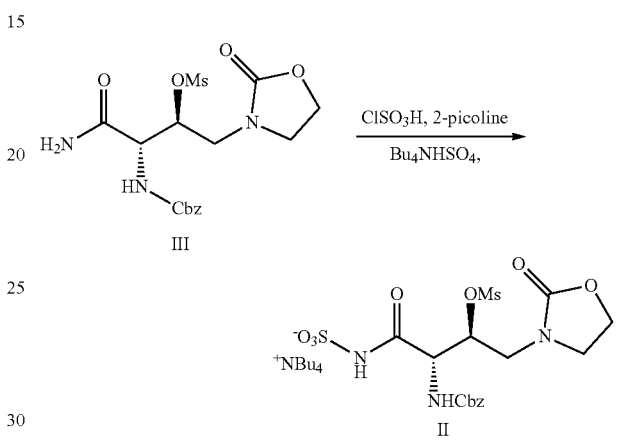

II

To a flask was added 2-picoline (11.50 g, 12.23 mL) and DMF (10 mL). The solution was cooled to 5° C., followed by slow addition of chlorosulfonic acid (7.20 g, 4.14 mL). The temperature was increased to 20° C. III (PG=Cbz, LG=$SO_2CH_3$) (5.13 g, 12.35 mmol) was added to the reaction mixture. The reaction mixture was heated to 42° C. for 18 h. IPC (in process control) showed complete conversion of starting material. The reaction was cooled to 20° C. and dropwise added to a solution of tetrabutylammonium hydrogen sulfate (4.6 g, 13.6 mmol) in the mixed solvents of dichloromethane (100 mL) and water (100 mL) at 5° C. The phases were separated and the water phase was extracted with dichloromethane (2*50 mL). The combined organic phase was washed with water (5*100 mL). The organic phase was concentrated to dryness and purified by column chromatography (dichloromethane/methanol=15/1 v/v) to afford II (PG=Cbz, LG=$SO_2CH_3$, $M^+$=$NBu_4^+$) (8.4 g, 92.30%), $^1$H NMR (400 MHz, CHLOROFORM-d) δ ppm 0.99 (t, J=7.34 Hz, 12H) 1.36-1.50 (m, 8H) 1.54-1.76 (m, 8H) 3.15 (br d, J=8.31 Hz, 2H) 3.21-3.35 (m, 8H) 3.47 (br dd, J=14.73, 7.27 Hz, 1H) 3.54-3.65 (m, 1H) 3.67-3.81 (m, 2H) 4.17-4.32 (m, 1H) 4.39-4.62 (m, 1H) 4.74 (br s, 1H) 5.11 (s, 3H) 5.32-5.50 (m, 1H) 6.47 (br s, 1H) 7.29-7.47 (m, 5H) 8.69-8.94 (m, 1H).

Synthesis of compound (IA)

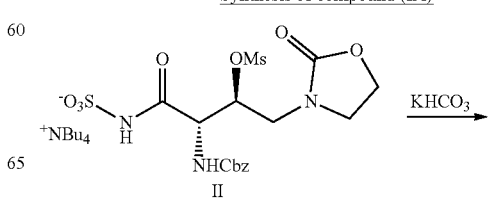

II

-continued

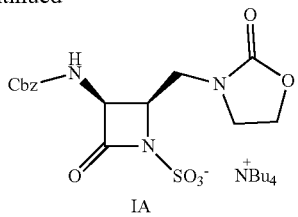

IA

A solution of II (PG=Cbz, LG=SO$_2$CH$_3$, M$^+$=NBu$_4^+$) (4.0 g) in dichloromethane (38 mL) was pumped to tube A at rate of 2.0844 mL/min, and a solution of KHCO$_3$ (3.0 g) in water (100 mL) was pumped to tube B at a rate of 1.4156 mL/min side to side. These two streams were mixed in a cross-mixer then flowed to a tube coil that was placed in an oil bath at 100° C. (FIG. 1). The residence time of the mixed stream in the coil was 2 min. The reaction mixture flowed through a back-pressure regulator that was set at ~7 bars, and was collected to a beaker. After completion of the collection, two phases was separated. The organic phase was concentrated to dryness. The residue was slurried in ethyl acetate (5 mL). The solid was filtered and the filter cake was dried to give IA (2.6 g, 75%), $^1$H NMR (400 MHz, CHLOROFORM-d) δ ppm 1.00 (t, J=7.27 Hz, 12H) 1.42 (sxt, J=7.31 Hz, 8H) 1.62 (quin, J=7.83 Hz, 8H) 3.13-3.39 (m, 8H) 3.54-3.69 (m, 2H) 3.81 (dd, J=14.98, 2.51 Hz, 1H) 3.96-4.13 (m, 1H) 4.22-4.47 (m, 3H) 4.99-5.23 (m, 3H) 6.42 (br d, J=9.29 Hz, 1H) 7.26-7.44 (m, 5H).

Synthesis of Compound 2A

Step 1

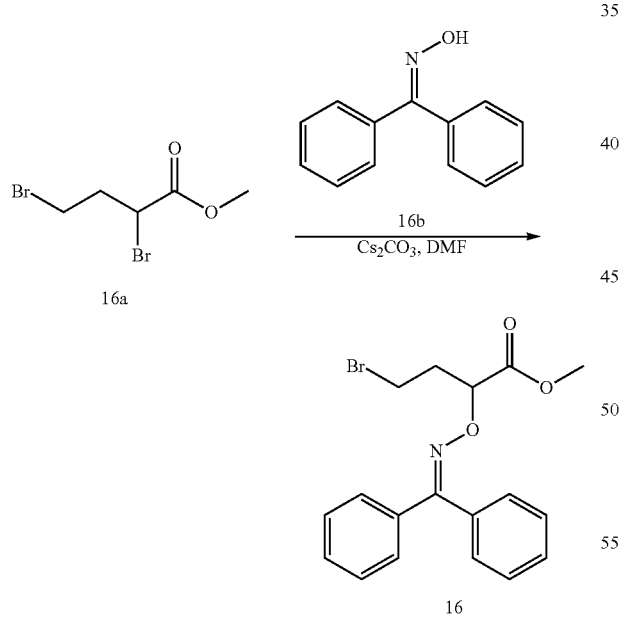

To a stirring solution of compound 16b (2 g, 10.14 mmol, 1.0 eq) in DMF (20 mL) was added Cs$_2$CO$_3$ (5.29 g, 16.22 mmol, 1.6 eq), then the resulting solution was stirred at room temperature for 10 mins, then compound 16a (5.27 g, 20.28 mmol, 2 eq) was added dropwise to the mixture for 2 minutes, then the resulting solution was stirred for another 2 hours. TLC showed the starting material was consumed completely. The mixture was added with water (60 mL) and extracted with MTBE (20 mL*3). The combined organic layers were dried over anhydrous sodium sulfate and concentrated. The crude was slurried in heptane to give 1.65 g 16 as a white solid (Yield: 57%), $^1$H NMR (400 MHz, DMSO-d$_6$) δ ppm 7.48-7.28 (m, 10H), 5.00-4.96 (t, J=6.0 Hz, 1H), 3.81 (s, 3H), 3.44-3.42 (m, 2H), 2.40-2.37 (m, 2H).

Step 2

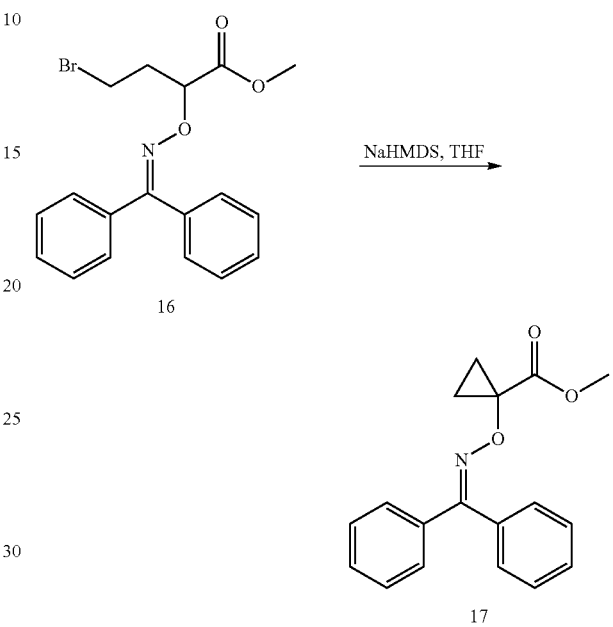

Compound 16 (1 g, 2.66 mmol, 1 eq) was dissolved in THF (20 mL) under Nitrogen, and cooled to −40° C. NaHMDS (1.6 mL, 2.0M THF solution, 1.2 eq) was added dropwise. The reaction was stirred for 1 h at −40° C. HPLC indicated the reaction was finished. The reaction was quenched with 10% Citric acid, extracted with MTBE (25 mL×2). The combined organic layers were washed with brine (30 mL), dried with Na$_2$SO$_4$, filtered and concentrated to give 17 as a yellow solid, which was used for the next step without purification (assay yield: 65%); $^1$H NMR (400 MHz, DMSO-d$_6$) δ ppm 7.27-7.13 (m, 10H), 3.46 (s, 3H), 1.21-1.17 (dd, J=7.2, 10.4 Hz, 2H); 1.14-1.11 (dd, J=7.2, 10.4 Hz, 2H).

Step 3

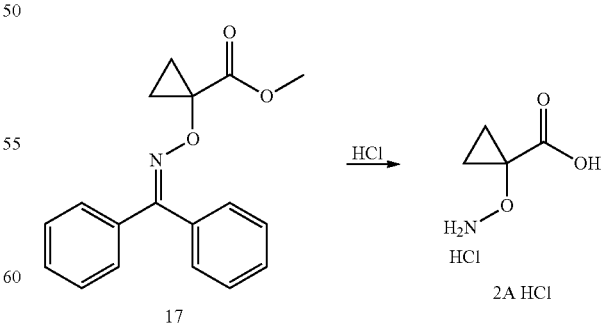

Compound 17 (100 mg) was dissolved in methanol (5 mL) and 2.0 M HCl IPAC solution (5 mL). The solution was heated at 45° C. for 3 days. HPLC indicated the reaction was finished. The reaction was cooled to room temperature and was diluted with 10 mL water. The reaction mixture was washed with MTBE (10 mL×2), organic layer was discarded and the aqueous layer was concentrated to give compound 2A HCl (32 mg, 62% yield), $^1$H NMR (400 MHz, DMSO-$d_6$) δ ppm 3.80-3.44 (br, 4H), 1.56 (s, 2H), 1.38 (s, 2H).

Step 4

To a solution of 2A HCl (0.70 g, 4.57 mmol) in methanol (5 mL) was added triethylamine (1.26 mL, 9.14 mmol) at room temperature. The solution was stirred for 20 min, and the solvent was removed under vacuum. To the residue was added IPAC (10 mL) leading to precipitation. The solid was filtered, and the filtrate was concentrated to provide 2A (0.50 g, 94% yield) containing ca. 6 wt % Et$_3$N—HCl.

Synthesis of Compound X From Compound of Formula (I), (IA)

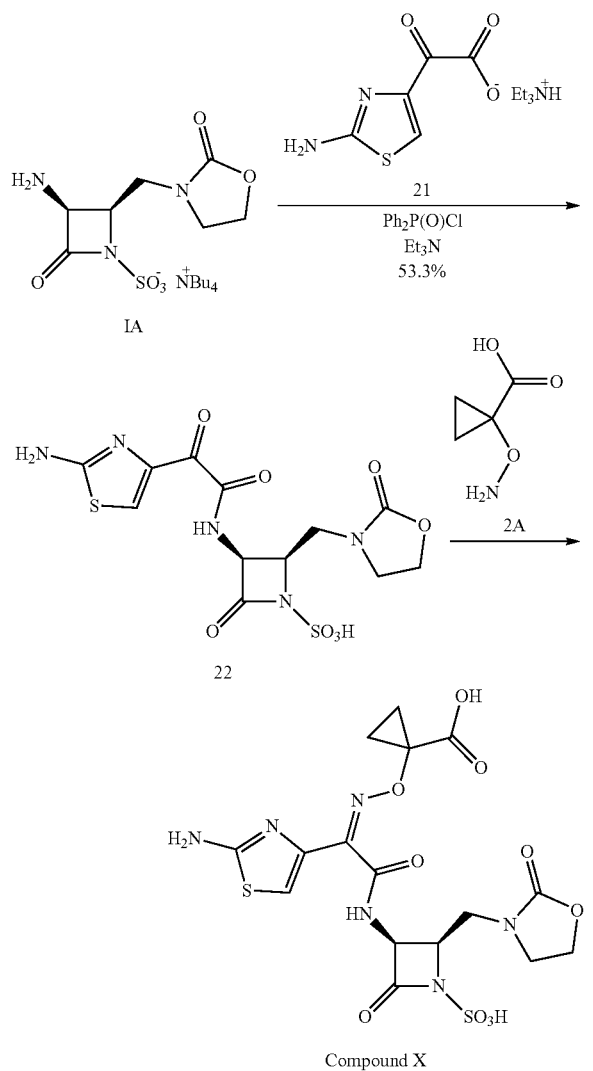

To a flask was charged 21 (1.00 g, 68.43 wt %, 2.50 mmol) and DMF (10 mL). The suspension was cooled to −20° C., to which was added diphenylphosphinic chloride (0.52 mL, 2.75 mmol). The solution was stirred at −20° C. for 30 min, followed by addition of a mixed solution of (IA) (1.52 g, 3.00 mmol) and triethylamine (0.52 mL, 3.76 mmol) in DMF (2 mL). The reaction mixture was stirred at 20° C. for 20 h, followed by addition of MTBE (20 mL). The reaction mixture was adjusted to pH=2-3 using aqueous HCl solution (37%). To the mixture was added isopropanol (100 mL). The resulting mixture was stirred for 4 h to obtain a suspension. The suspension was filtered and the filter cake was dried under vacuum to afford crude 22 (1.17 g). The crude 22 was slurried in a combined solvent of THF/H$_2$O (=12 mL/3 mL), and filtered to afford 22 (0.744 g, 75 wt % by Q-NMR, 53.3% yield). $^1$H NMR (400 MHz, DMSO-$d_6$) δ ppm 3.47-3.55 (m, 2H) 3.59-3.63 (m, 2H) 4.13-4.21 (m, 3H) 5.05 (dd, J=8.8, 5.6 Hz, 1H) 8.22 (s, 1H) 9.73 (d, J=8.7 Hz, 1H).

To a suspension of 22 (580 mg, 75 wt %, 1.037 mmol) in DMAC (1.5 mL) was added 2A (214.3 mg, 85 wt %, 1.556 mmol). The reaction was stirred at 25° C. for 3 days, and in process control showed 22/Compound X=4/96, and Z/E=91/9. the mixture was slowly added into 15 ml acetone to precipitate yellowish solid. The reaction mixture was filtered to afford Compound X (0.7 g, 34 wt % by QNMR, 44% yield).

Synthesis of Compound 3 (R$^2$=CH(Ph)$_2$)

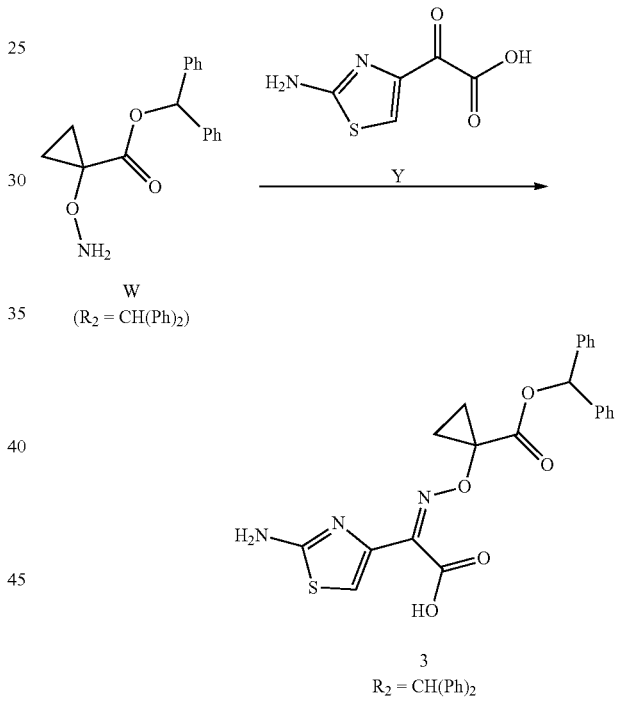

2-(2-aminothiazol-4-yl)-2-oxoacetic acid (Y) (10.00 g, 47.93 mmol) and compound W (R$^2$=CH(Ph)$_2$) (13.31 g, 46.98 mmol) were suspended in DMAC (40 mL), followed by addition of triethylamine (5.01 mL, 35.95 mmol). The reaction mixture was stirred at 20° C. for 5 h. HPLC showed completion of the reaction, and Z/E=97/3. To the reaction mixture was added water (120 mL) with stirring. The mixture was stirred for 20 min to obtain a suspension. The suspension was filtered and the filter cake was washed with water (50 mL). The filter cake was slurried in a combined solvent of THF/ethyl acetate (50 mL/50 mL) at 60° C. and cooled to 20° C. The solid was filtered and dried at 50° C. for 3 h to get 3 (R$^2$=CH(Ph)$_2$) (19.5 g, 88% yield). $^1$H NMR (400 MHz, DMSO-$d_6$) δ ppm 1.37-1.42 (m, 2H) 1.44-1.49 (m, 2H) 6.87 (s, 1H) 6.94 (s, 1H) 7.22-7.30 (m, 6H) 7.45-7.49 (m, 4H).

Alternative Synthesis of Compound X From Compound of Formula (I), (IA)

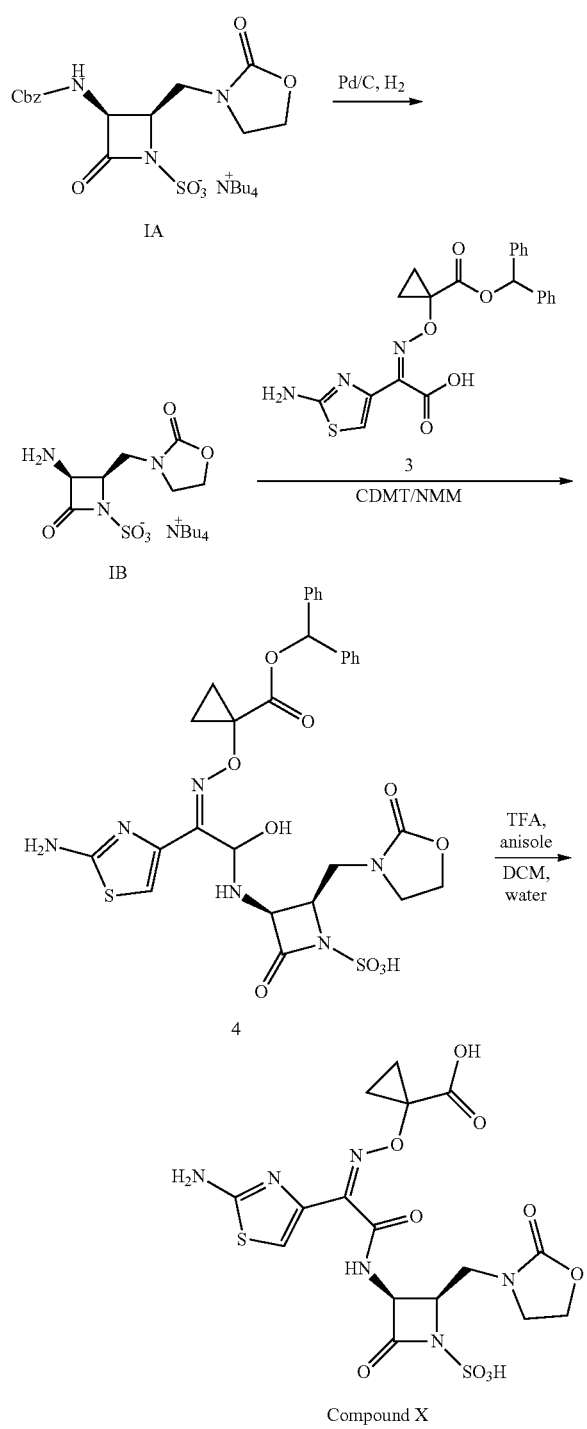

IA (40.14 g, 62.63 mmol) was dissolved in methanol (200 mL), followed by addition of Pd/C (10%, 1.1 g). The reaction mixture was maintained under hydrogen atmosphere (1~2 bar) at 20° C. for 24 h. In process control showed completion of the reaction. The reaction mixture was filtered. The filtrate was concentrated to give an oil of IB ($M^+=NBu_4^+$) (58.20 g, 55 wt % by Q-NMR, 100% yield). $^1$H NMR (400 MHz, DMSO-$d_6$) δ ppm 0.93 (t, J=7.3 Hz, 12H) 1.23-1.36 (m, 8H) 1.57 (m, 8H), 2.99-3.28 (m, 8H) 3.37 (dd, J=14.3, 7.5 Hz, 1H) 3.65-3.70 (m, 3H) 3.84-3.88 (m, 1H) 4.08 (d, J=5.6 Hz, 1H) 4.18-4.22 (m, 2H).

3 ($R^2$=CH(Ph)$_2$) (0.95 g, 2.17 mmol) was dissolved in THF (20 mL). To the solution was added N-methyl morpholine (0.77 g, 7.60 mmol) and 2-chloro-4,6-dimethoxy-1,3,5-triazine (0.57 g, 3.26 mmol). The reaction mixture was stirred at 20° C. for 1 h followed by addition of IB ($M^+=NBu_4^+$) (2.70 g, 48.98 wt %, 2.61 mmol). The reaction was stirred at 20° C. for 5 h. In process control showed completion of the reaction. To the reaction mixture was added ethyl acetate (20 mL). The organic phase was washed with brine (10 mL). Solvent was removed. Acetone (40 ml) was added to dissolve residue. TFA (1.24 g, 10.86 mmol) dissolved in acetone (3 ml) was added slowly. The white solid was filtered and washed by acetone (10 ml) two times. Dried at 40° C. for 5 h to get compound 4 ($R^2$=CH(Ph)$_2$). $^1$H NMR (400 MHz, DMSO-$d_6$) δ ppm 1.49-1.55 (m, 4H) 3.27 (dd, J=14.4, 6.2 Hz, 1H) 3.49-3.65 (m, 2H) 3.71 (dd, J=14.4, 6.2 Hz, 1H) 4.04-4.10 (m, 1H) 4.07 (dd, J=16.0, 8.6 Hz, 1H) 4.17 (dd, J=11.8, 6.0 Hz, 1H) 5.28 (dd, J=9.0, 5.7 Hz, 1H) 6.88 (s, 1H) 7.03 (s, 1H) 7.18-7.32 (m, 6H) 7.43 (m, 4H) 9.45 (d, J=9.0 Hz, 1H).

Crude 4 ($R^2$=CH(Ph)$_2$) (2.13 g) was dissolved in dichloromethane (20 mL). The solution was cooled to 0° C. To the solution was added anisole (0.68 mL, 6.24 mmol) and trifluoroacetic acid (2.16 mL, 28.08 mmol). The reaction was warmed to 20° C., and stirred for 15 h. In process control showed completion of the reaction. The aqueous phase was separated and added to acetone (40 mL) to obtain a suspension. The suspension was filtered to afford Compound X (0.98 g, 54.5% yield over two steps). $^1$H NMR (400 MHz, DMSO-$d_6$) δ ppm 1.40 (m, 4H) 3.26 (dd, J=14.4, 6.0 Hz, 1H) 3.54-3.69 (m, 3H) 4.14-4.21 (m, 3H) 5.25 (dd, J=8.9, 5.7 Hz, 1H) 7.02 (s, 1H) 9.38 (d, J=9.0 Hz, 1H).

The invention claimed is:

1. A process for the preparation of Compound X or a salt thereof, or a solvate or hydrate thereof, comprising the step of reacting a compound of formula 22, or a salt thereof, with a compound of formula 2A, or a salt thereof

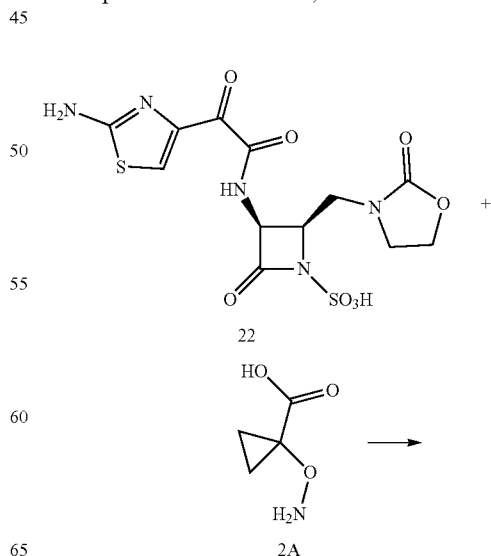

-continued

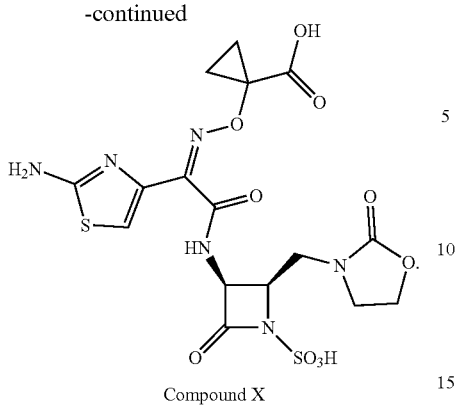

Compound X

2. A process for the preparation of compound 22, or a salt thereof, comprising the step of reacting a compound of formula (IB) with the compound of formula 21

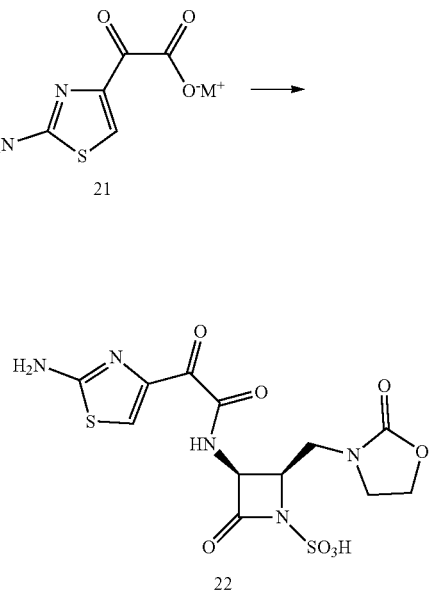

in the presence of a solvent, with a base and a coupling agent, wherein M⁺ is hydrogen or a salt forming cation.

3. A process for the preparation of Compound X or a salt thereof, or a solvate or hydrate thereof, comprising preparation of compound 22, or a salt thereof, comprising the step of reacting a compound of formula (IB) with a compound of formula 21

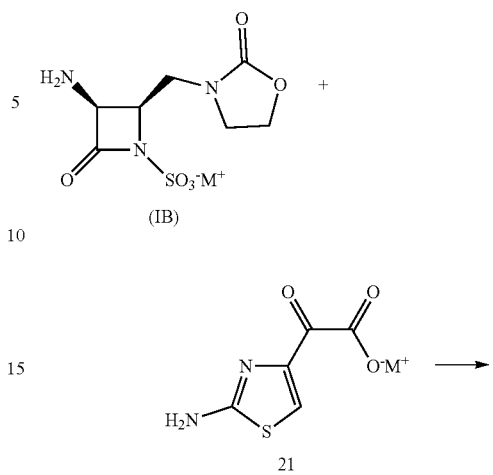

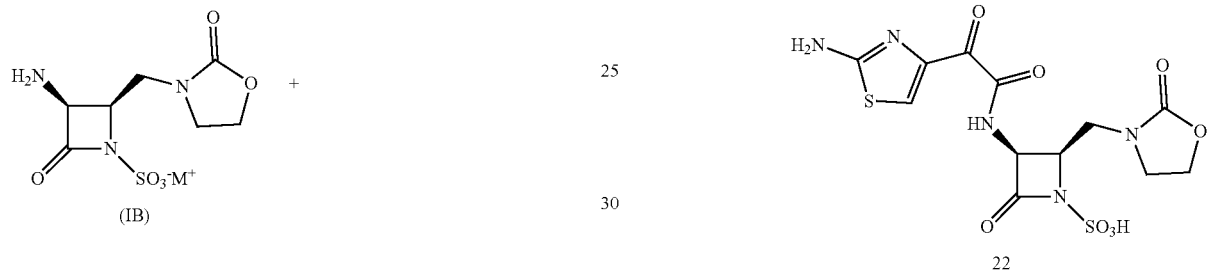

in the presence of a solvent, with a base and a coupling agent, wherein M⁺ is hydrogen or a salt forming cation, and reacting compound 22 with compound 2A according to claim 1.

4. The process of claim 2, wherein the solvent comprises one or more solvents selected from the group consisting of tetrahydrofuran, 1,2-dimethoxyethane, dimethylformamide, dimethylacetamide, aromatic hydrocarbon, acetonitrile, 2-methyltetrahydrofuan, and water, or a mixture thereof.

5. The process according to claim 2, wherein the base is selected from the group consisting of $K_2CO_3$, $Cs_2CO_3$, $K_3PO_4$, DIPEA, NMM, DMAP, and $Et_3N$.

6. The process according to claim 2, wherein the coupling agent is one or more coupling agents selected from the group consisting of N,N'-carbonyldiimidazole, ethyl chloroformate, 2-ethoxyl-ethoxycarbonyl-1,2-dihydroquinoline (EEDQ), isobutyl chloroformate, isopropenyl chloroformate, trimethylacetyl chloride, 2,4,6-trichlorobenzoyl chloride, isobutyl chloroformate, 4-nitrophenyl chloroformate, cyanuric chloride, oxalyl chloride, dimethylformamide/$POCl_3$ (Vilsmeier's reagent), N-Ethyl-N'-(3-dimethylaminopropyl)carbodiimide (EDC), organophosphorus reagents, 2-Chloro-4,6-dimethoxy-1,3,5-triazine (CDMT), 2-bromo-1-ethyl-pyridinium tetrafluoroborate (BEP), tri(dimethylamino)benzotriazol-1-yloxyphosphonium hexafluorophosphate (BOP), and 7-azabenzotriazol-1-yloxytris (dimethylamino)phosphonium hexafluorophosphate (AOP).

7. The process of claim 2, wherein the compound of formula (IB) is prepared from a compound of formula (I) comprising the step of deprotection of a compound of formula (I),

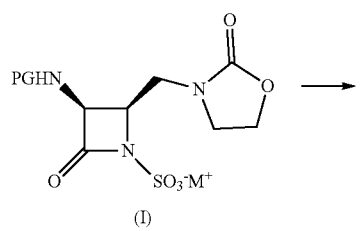

(I)

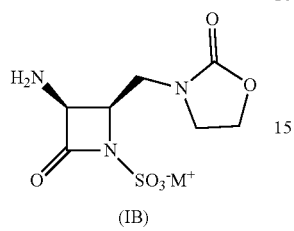

(IB)

wherein PG is a nitrogen protecting group, M⁺ is hydrogen or a salt forming cation.

8. The process of claim 7, wherein the nitrogen protecting group PG is benzyloxycarbonyl, fluorenylmethyloxycarbonyl, allyloxycarbonyl, or benzyl.

9. The process according to claim 7, wherein deprotection of the compound of formula (I) is carried out by reduction in the presence of a catalyst and hydrogen, wherein the catalyst is selected from the group consisting of Raney nickel, Pt/C, Rh/C, Pd/Al$_2$O$_3$, Pd/CaCO$_3$, RhCl(PPh$_3$)$_3$, Lindlar catalyst, PtO$_2$, Pd/C, [Rh(cod)(PPh$_3$)$_2$]⁺, [Ir(cod)(PCy$_3$)(Py)]⁺, Pd(OH)$_2$, Pd(OAc)$_2$, Pd$_2$(dba)$_3$, Zn, Fe, Sm, NiCl$_2$, Ni(OAc)$_2$, CoCl$_2$, ZrCl$_4$, and TiCl$_3$.

10. The process of claim 9, wherein the catalyst is Pd/C.

11. The process according to claim 7, wherein the nitrogen protecting group PG is benzyloxycarbonyl.

12. The process of claim 7, wherein the compound of formula (I) is of formula (IA),

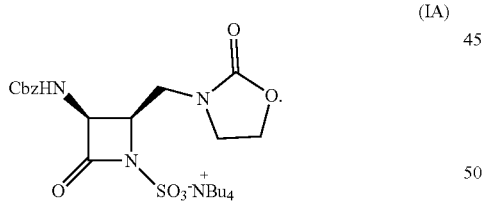

(IA)

13. A process for preparing Compound X, or a salt thereof, or a solvate or hydrate thereof, the process comprising the steps of:

(a-1) preparing

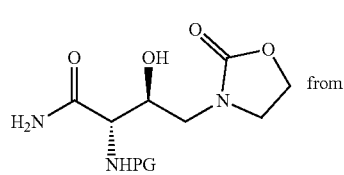

(IV)

from

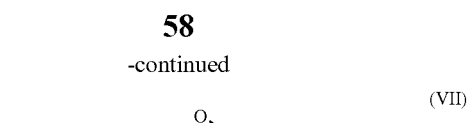

(VII)

by reducing the compound of formula (VII) under asymmetric reduction conditions to produce a compound of formula (VIIc),

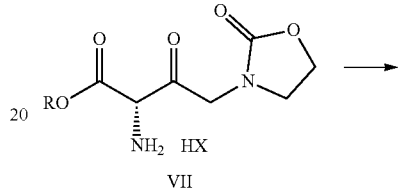

VII

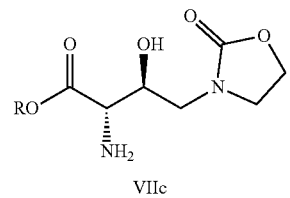

VIIc or a salt thereof, wherein PG is a nitrogen protecting group, R is branched or linear C$_1$-C$_7$ alkyl, benzyl, or C$_1$-C$_4$-alkoxy substituted benzyl, and X is selected from the group consisting of halide, carboxylate, and sulfonate; and protecting the NH$_2$ group in the compound of formula (VIIc), to produce a compound of formula (VIIe),

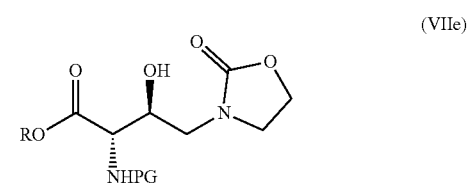

(VIIe)

wherein PG is a nitrogen protecting group and R is branched or linear C$_1$-C$_7$ alkyl, benzyl, or C$_1$-C$_4$-alkoxy substituted benzyl, and reacting a compound of formula (VIIe) with a source of ammonia to obtain the compound of formula (IV);

(b-1) preparing

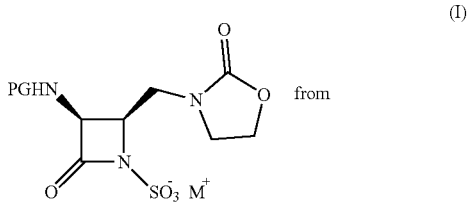

(I)

from

-continued

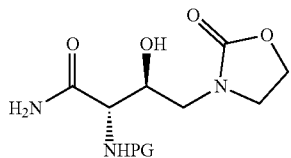
(IV)

by converting the compound of formula (IV) to a compound of formula (III),

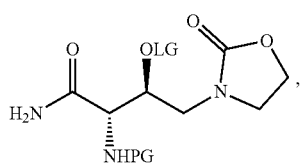
(III)

wherein PG is a nitrogen protecting group, LG is —SO$_2$T, wherein T is selected from C$_4$F$_9$, CF$_3$, F, C$_6$H$_4$CH$_3$, CH$_3$, and C$_6$H$_6$, reacting the compound of formula (III), in a solvent with a base, followed by addition of a halosulfonic acid and a salt forming reagent, to produce a compound of formula (II),

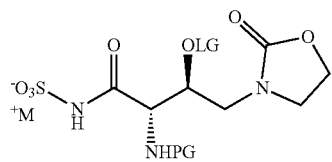
(II)

wherein M$^+$ is hydrogen or a salt forming cation, and LG and PG are as defined for a compound of formula (III), and
reacting the compound of formula (II) in a solvent with a base to produce the compound of formula (I); and
(c-1) reacting

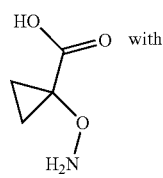
2A with

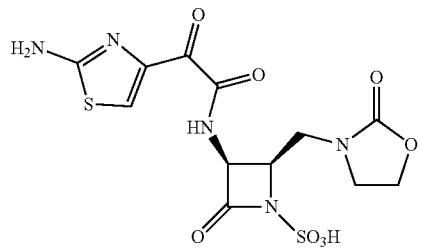
22 to form Compound X, wherein compound 22 is obtained according to claim 2.

14. A compound of formula (IA)

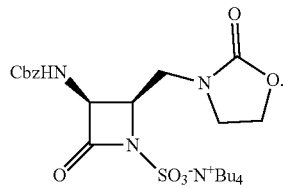
(IA)

15. A compound of formula (4)

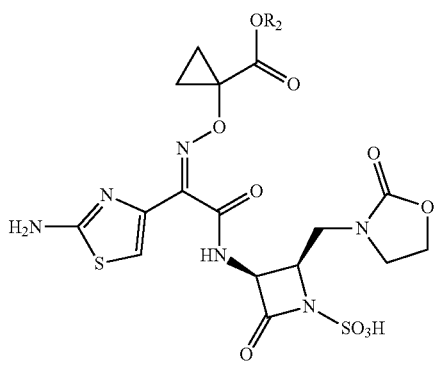
4 wherein R$^2$ is selected from the group consisting of branched or linear C$_1$-C$_7$-alkyl, benzyl, C$_1$-C$_4$-alkoxy substituted benzyl, and CH(aryl)$_2$.

16. A compound of formula (22)

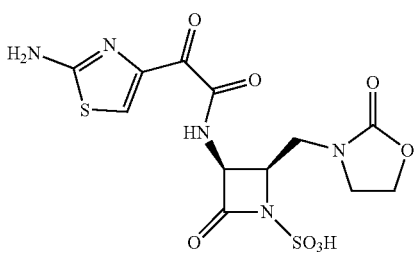
22 or a salt thereof.

17. A compound of formula (2A)

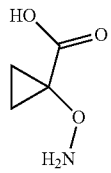
2A or a salt thereof.

* * * * *